United States Patent
Chen et al.

(10) Patent No.: US 8,044,350 B2
(45) Date of Patent: Oct. 25, 2011

(54) MINIATURIZED ULTRAFINE PARTICLE SIZER AND MONITOR

(75) Inventors: Da-Ren Chen, St. Louis, MO (US); Chaolong Qi, Cincinnati, OH (US)

(73) Assignee: Washington University, St. Louis, MO (US)

( * ) Notice: Subject to any disclaimer, the term of this patent is extended or adjusted under 35 U.S.C. 154(b) by 501 days.

(21) Appl. No.: 12/325,884

(22) Filed: Dec. 1, 2008

(65) Prior Publication Data

US 2010/0001184 A1   Jan. 7, 2010

Related U.S. Application Data

(60) Provisional application No. 60/991,079, filed on Nov. 29, 2007.

(51) Int. Cl.
*H01J 49/00* (2006.01)

(52) U.S. Cl. ......... 250/293; 250/281; 250/282; 250/288

(58) Field of Classification Search .......... 250/281–284, 250/288, 290, 292, 293; 73/28.01, 28.02, 73/28.04, 28.05
See application file for complete search history.

(56) References Cited

U.S. PATENT DOCUMENTS

| | | | |
|---|---|---|---|
| 3,958,962 A | 5/1976 | Hayashi | |
| 3,980,455 A | 9/1976 | Masuda | |
| 4,108,615 A | 8/1978 | Satterhwaite | |
| 4,265,641 A | 5/1981 | Natarajan | |
| 4,414,603 A | 11/1983 | Masuda | |
| 4,431,434 A | 2/1984 | Rinard et al. | |
| 4,449,159 A | 5/1984 | Schwab et al. | |
| 4,539,022 A | 9/1985 | McLoughlin | |
| 5,158,580 A | 10/1992 | Chang | |
| 5,395,430 A | 3/1995 | Lundgren et al. | |
| 5,475,228 A | 12/1995 | Palathingal | |
| 5,973,904 A | 10/1999 | Pui et al. | |
| 5,992,244 A | 11/1999 | Pui et al. | |
| 6,145,391 A | 11/2000 | Pui et al. | |
| 6,905,029 B2 | 6/2005 | Flagan | |
| 7,031,133 B2 | 4/2006 | Riebel et al. | |
| 7,201,879 B2 | 4/2007 | Hill et al. | |
| 7,812,306 B2 * | 10/2010 | Fissan et al. .................. 250/288 |

(Continued)

OTHER PUBLICATIONS

Knutson, E.O., Whitby, K.T., Aerosol Classification by Electric Mobility: Apparatus, Theory, and Applications. Journal of Aerosol Science, 1975, pp. 443-451, vol. 6., Pergamon Press, Great Britain.

(Continued)

*Primary Examiner* — Michael Maskell
(74) *Attorney, Agent, or Firm* — Armstrong Teasdale LLP

(57) ABSTRACT

An apparatus for measuring particle size distribution includes a charging device and a precipitator. The charging device includes a corona that generates charged ions in response to a first applied voltage, and a charger body that generates a low energy electrical field in response to a second applied voltage in order to channel the charged ions out of the charging device. The corona tip and the charger body are arranged relative to each other to direct a flow of particles through the low energy electrical field in a direction parallel to a direction in which the charged ions are channeled out of the charging device. The precipitator receives the plurality of particles from the charging device, and includes a disk having a top surface and an opposite bottom surface, wherein a predetermined voltage is applied to the top surface and the bottom surface to precipitate the plurality of particles.

18 Claims, 33 Drawing Sheets

U.S. PATENT DOCUMENTS

2006/0110818 A1    5/2006    Hill et al.
2006/0187609 A1    8/2006    Dunn

OTHER PUBLICATIONS

Koch, W., Dunkhorst, W., Lodding., Design and Performance of a New Personal Aerosol Monitor, Aerosol Science and Technology, 1999, pp. 231-246, vol. 31, American Association of Aerosol Research, Taylor & Francis, Germany.

Kruis, F. E., and Fissan H., Nanoparticle Charging in a Twin Hewitt Charger, Journal of Nanoparticle Research, 2001, pp. 39-50, Kluwer Academic Publishers, Netherlands.

Lee, S. J., Demokritou, P., Koutrakis, P., Delgado-Saborit, J.M., Development and Evaluation of Personal Respirable Particulate Sampler (PRPS), Atmospheric Environment, 2006, pp. 212-224, vol. 40, Elsevier Ltd., USA.

Liu, L. J., Slaughter, J. C. Larson, T. V., Comparison of Light Scattering Devices and Impactors for Particulate Measurements in Indoor, Outdoor, and Personal Environments, Environmental Science & Technology, 2002, pp. 2977-2986, vol. 36, American Chemical Society Publications, USA.

Mader, B. T., Flagan, R. C., Seinfeld, J. H. Sampling Atmospheric Carbonaceous Aerosols Using a Particle Trap Impactor/Denuder Sampler, Environmental Science & Technology, 2001, pp. 4857-4867, vol. 35, American Chemical Society Publications, USA.

Maynard, A. D., Kuempel, E. D., Airborne Nanostructured Particles and Occupational Health, Journal of Nanoparticle Research, 2005, pp. 587-614, vol. 7, Springer, USA.

Misra, C., Singh, M., Shen, S., Sioutas, C., Hall, P. M., Development and Evaluation of a Personal Cascade Impactor Sampler (PCIS), Journal of Aerosol Science, 2002, pp. 1027-1047, vol. 33, Pergamon Press-Elsevier Ltd., USA.

Oberdorster, G., Oberdorster, E., Oberdorster, J., Nanotoxicology: An Emerging Discipline Evolving from Studies of Ultrafine Particles, Environmental Health Perspectives, 2005, pp. 823-839, vol. 113.

Qi, C., Chen, D. R., and Pui, D. Y. H., Experimental Study of a New Corona-Based Unipolar Aerosol Charger, Journal of Aerosol Science, 2007, pp. 775-792, vol. 38, Elsevier Ltd., USA.

Reischl, G. P., Makela, J. M., Karch, R., and NECID, J., Bipolar Charging of Ultrafine Particles in the Size Range Below 10 nm., Journal of Aerosol Science, 1996, pp. 931-949, vol. 27, Pergamon Press-Elsevier Ltd., Great Britain.

Romay, F. J. and Pui D. Y. H., Unipolar Diffusion Charging of Aerosol Particles at Low Pressure, Aerosol Science and Technology, 1991, pp. 60-68, vol. 15, Elsevier Science Publishing Co., USA.

Romay, F. J. and Pui D. Y. H., On the Combination Coefficient of Positive Ions with Ultrafine Neutral Particles in the Transition and Free-Molecule Regime, Aerosol Science and Technology, 1992, pp. 134-147, vol. 17, Elsevier Ltd., USA.

Scheibel, H. G. and J. Porstendorfer, Generation of Monodisperse Ag-and NaCl-Aerosol with Particle Diameters Between 2 and 300 nm., Journal of Aerosol Science, 1983, pp. 113-126, vol. 14, No. 2, Pergamon Press, Great Britain.

Wang, S. C., and Flagan, R. C., Scanning Electrical Mobility Spectrometer, Aerosol Science and Technology, Jan. 1, 1990, pp. 230-240, vol. 13:2, Elsevier Science Publishing, USA.

Warheit, D. B., Nanoparticles: Heath Impacts, Materials Today, Feb. 2004, pp. 32-35, vol. 7, Elsevier Ltd., USA.

Wiedensohler, A., An Approximation of the Bipolar Charge Distribution for Particles in the Submicron Size Range, Journal of Aerosol Science, 1988, pp. 387-389, vol. 19, No. 3, Pergamon Press, Great Britain.

Hoppel, W. A. and Frick, G. M., Ion-Aerosol Attachment Coefficients and the Steady-Stake Charge Distribution on Aerosols in a Bipolar Ion Environment, Aerosol Science and Technology, 1986, pp. 1-21, vol. 5, Elsevier Science Inc., USA.

Forsyth, B., Liu, B. Y. H., Romay, F. J., Particle Charge Distribution Measurement for Commonly Generated Laboratory Aerosols, Aerosol Science and Technology, 1998, pp. 489-501, vol. 28, American Association for Aerosol Research, Elsevier Science Inc., USA.

Flagan, R.C., Opposed Migration Aerosol Classifier (OMAC), Aerosol Science and Technology, 2004, pp. 890-899, vol. 38, American Association for Aerosol Research, USA.

Flagan, R.C., History of Electrical Aerosol Measurements, Aerosol Science and Technology, 1998, pp. 301-380, vol. 28, Elsevier Science Inc., USA.

Dreher, K. L., Health and Environmental Impact of Nanotechnology: Toxicological Assessment of Manufactured Nanoparticles, Toxicological Sciences, 2004, pp. 3-5, vol. 77 (1), Society of Toxicology, USA.

Chen D-R. and Pui D. Y. H., A High Efficiency, High Throughput Unipolar Aerosol Charger for Nanoparticles, Journal of Nanoparticle Research, 1999, pp. 115-126, vol. 1, Kuwer Academic Publishers, Nertherlands.

Chen, C-C. and Huang, S-H., Lin, W-Y., Shih, T-S., Jeng, F-T., The Virtual Cyclone as a Personal Respirable Sampler, Aerosol Science and Technology, 1999, pp. 422-432, vol. 31, American Association for Aerosol Research, Taylor & Francis, UK.

Buscher, P., Schmidt-Ott, A. and Wiedensohler A., Performance of a Unipolar 'Square Wave' Diffusion Charger with Variable nt-Product, Journal of Aerosol Science, 1994, pp. 651-663, vol. 25, Pergamon Press-Elsevier Ltd, Great Britain.

Boisdron, Y. and Brock, J. R., On the Stochastic Nature of the Acquisition of Electrical Charge and Radioactivity by Aerosol Particles, Atmospheric Environment, 1970, pp. 35-50, vol. 4, Pergamon Press, Great Britain.

Biswas, P., Wu, C. Y., Nanoparticles and the Environment, Journal of Air & Waste Management Association, 2005, pp. 708-746, vol. 55.

Alguacil, F. J., and Alonso, M. A., Multiple Charging of Ultrafine Particles in a Corona Charger, Journal of Aerosol Science, 2006, pp. 875-884, vol. 37 No. 2, Elsevier, Ltd., USA.

Adachi, M., Liu, B. Y. H., and Pui, D. Y. H., Development of an Automatic System for Measuring Particle Charge and Size Distribution in a Clean Room, Part. Part. Syst. Charact., 1991, pp. 200-208, vol. 8, VCH Verlagsgesllshaft.

Adachi, M., Y. Kousaka and K. Okuyama, Unipolar and Bipolar Diffusion Charging of Ultrafine Aerosol Particles, Journal of Aerosol Science, 1985, pp. 109-123, vol. 16 No. 2, Pergamon Press, Great Britain.

Kauppinen, El, Coal Combustion Aerosols—A Field Study, Environmental Science & Technology, 1990, pp. 1811-1818, vol. 24, American Chemical Society, USA.

Hernandez-Sierra, F.J., Alguacil, M. Alonso, Unipolar Charging of Nanometer Aerosol Particles in a Corona Ionizer, Journal of Aerosol Science, 2003, pp. 733-745, vol. 34, Pergamon Press-Elsevier Science Ltd. USA.

* cited by examiner

Aerosol Outlet

Tungsten needle

Spherical porous cage

Aerosol Inlet

+HV

Ion Driven Voltage 0.5

Aerosol Inlet →

Aerosol Outlet →

FIG. 19

Aerosol Inlet → Aerosol Outlet →

MINIATURIZED ULTRAFINE PARTICLE SIZER AND MONITOR

CROSS REFERENCE TO RELATED APPLICATIONS

This application claims the benefit of U.S. Provisional Application No. 60/991,079 filed Nov. 29, 2007, which is hereby incorporated by reference in its entirety.

STATEMENT REGARDING FEDERALLY SPONSORED RESEARCH & DEVELOPMENT

This invention was made with government support under grant NAG3-2625 awarded by the NASA Glenn Research Center. The government may have certain rights in the invention.

BACKGROUND

The subject matter disclosed herein relates generally to monitoring particles and, more particularly, to monitoring exposure to small particles, such as nanoparticles, using miniaturized personal devices.

Particles in the submicron and nanometer size range have been reported in the exhausts of different combustion sources, chemical processes and aerosol reactors. Examples include the exhausts of diesel and jet engines, the emission from coal-combustion power plants, and welding fumes. Such nanoparticulate matter is considered environmental pollution, and thus harmful. Separately, many modern industrial applications have begun to utilize nanoparticles as part of a growing technology. For example, the photocatalysis of nano-sized $TiO_2$ has been proposed or implemented for many practical applications including bacteria sterilization, oxidation of soot particles, decomposition of kitchen oils, super-hydrophilic surface coating, and hydrogen production. Nanoparticles of different materials are synthesized in chemical reactors for a variety of modern industrial, and are the building blocks for the recent national initiative in nanotechnology in the United States. Meanwhile, the number of scientific publications on the toxicity of newly synthesized nanoparticles is increasing. Workers in current and future nanotechnology-related manufacturing facilities are increasingly likely to be exposed to nanoparticles. Low-cost, miniaturized personal devices for monitoring exposure to nanoparticles are lacking in the art.

BRIEF DESCRIPTION

In one aspect, an apparatus for measuring particle size distribution is provided. The apparatus includes a charging device and a precipitator. The charging device includes a corona tip and a charger body. The corona tip generates charged ions in response to a first applied voltage, and the charger body generates a low energy electrical field in response to a second applied voltage to channel the charged ions out of the charging device in a direction. The corona tip and the charger body are arranged relative to each other in order to direct a flow of a plurality of particles through the low energy electrical field in a substantially parallel direction relative to the direction of the charged ions being channelled out of the charging device. The precipitator receives the plurality of particles from the charging device, and includes a disk having a top surface and an opposite bottom surface. A predetermined voltage is applied to the top surface and the bottom surface to precipitate the plurality of particles.

In another aspect, a method is provided for assembling a particle size measurement device. The method includes providing a charging device that includes a corona tip and a charger body, wherein the corona tip is configured to generate charged ions in response to a first applied voltage. The charger body is configured to generate a low energy electrical field in response to a second applied voltage in order to channel the charged ions out of the charging device in a direction, and the corona tip and the charger body are arranged relative to each other to direct a flow of a plurality of particles through the low energy electrical field in a substantially parallel direction relative to the direction of the charged ions being channelled out of the charging device. The method also includes coupling a precipitator to an outlet of the charging device to receive the plurality of particles, wherein the precipitator includes a disk having a top surface and an opposite bottom surface. A predetermined voltage is applied to the top and bottom surfaces to precipitate the plurality of particles.

In another aspect, a method is provided for measuring particle size distribution. The method includes generating charged ions in response to a first voltage applied to a corona tip within a charging device, and generating a low energy electrical field in response to a second voltage applied to a charger body coupled to the corona tip within the charging device in order to channel the charged ions out of the charging device in a direction. The corona tip and the charger body are arranged relative to each other to direct a flow of a plurality of particles through the low energy electrical field in a substantially parallel direction relative to the direction of the charged ions being channelled out of the charging device. The method also includes receiving the plurality of particles from the charging device in a precipitator that includes a disk having a top surface and an opposite bottom surface, and applying a predetermined voltage to the top surface and the bottom surface in order to precipitate the plurality of particles.

BRIEF DESCRIPTION OF THE DRAWINGS

The embodiments described herein may be better understood by referring to the following description in conjunction with the accompanying drawings.

FIG. 3 is a schematic diagram of a unipolar aerosol mini-charger that may be used with the mini-nanoparticle sizers shown in FIGS. 1 and 2.

FIG. 6 is a schematic diagram of another alternative embodiment of a mini-charger that may be used with the mini-nanoparticle sizers shown in FIGS. 1 and 2.

FIG. 10 also illustrates data calculated by the birth-and-death charging model with the ion-particle combination coefficient calculated from the Fuchs limiting sphere charging theory.

FIG. 19 is a schematic diagram of an alternative embodiment of a mini-disk classifier that may be used with the mini-nanoparticle sizers shown in FIGS. 1 and 2.

FIG. 20 is a schematic diagram of a second alternative embodiment of a mini-disk classifier that may be used with the mini-nanoparticle sizers shown in FIGS. 1 and 2.

FIG. 21 is a schematic diagram of a third alternative embodiment of a mini-disk classifier that may be used with the mini-nanoparticle sizers shown in FIGS. 1 and 2.

DETAILED DESCRIPTION

Figure 1:
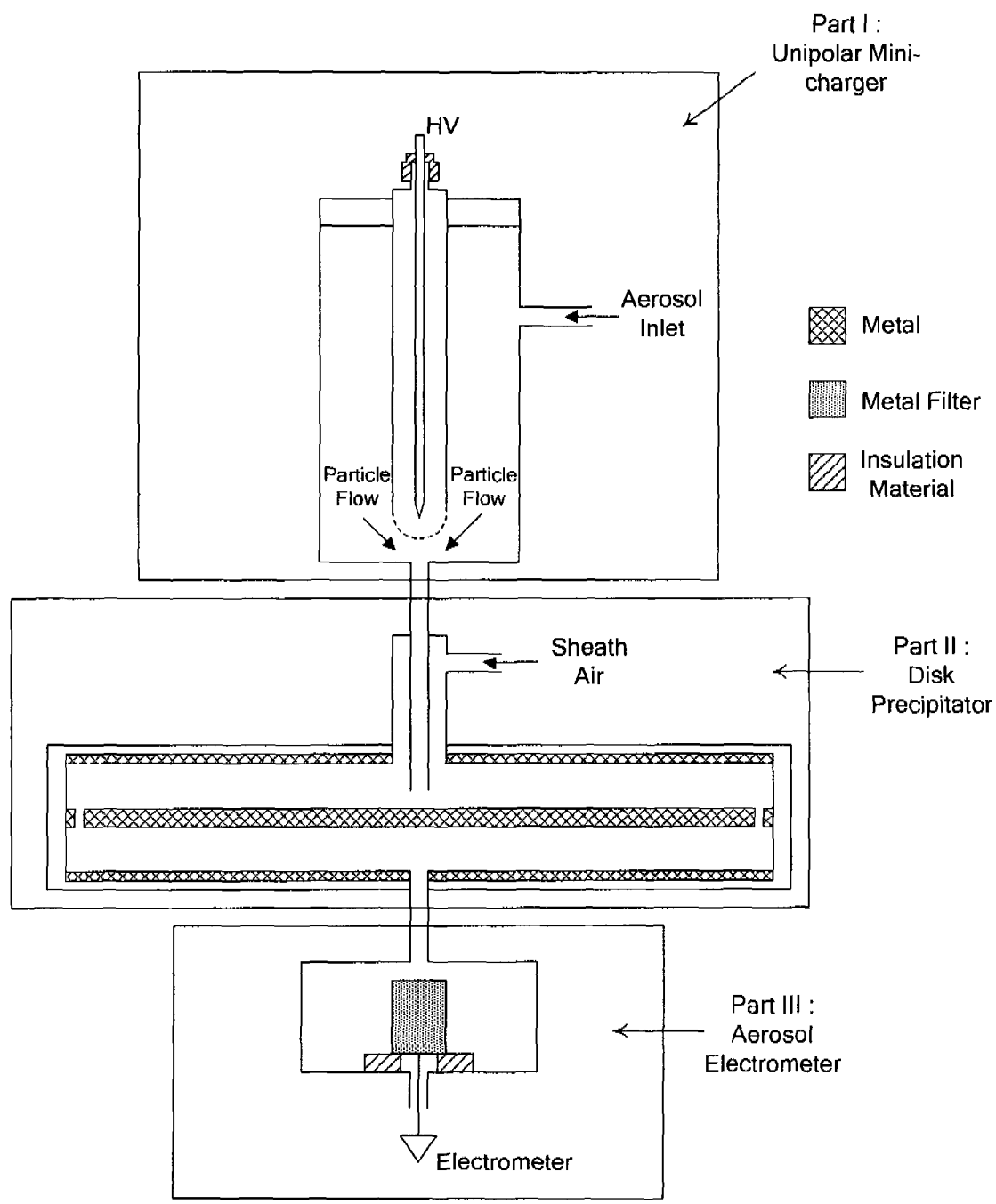
FIG. 1 is a schematic diagram of a mini-nanoparticle sizer in accordance with the current invention.

Embodiments of the invention include a mini-electrostatic sizer having a unipolar mini-charger, a disk precipitator, and a miniaturized aerosol electrometer. The sizer enables the monitoring and/or measurement of the variation of ultrafine particle (e.g., nanoparticle) size distributions as a function of space and time. In an embodiment, the sizer functions as a personal dosimeter.

Existing particle instruments for measuring particle size distribution in the supermicron and larger submicron size range are mainly used in scientific studies. However, such existing instruments are bulky and expensive, which limits their application in the industrial hygiene area. The existing personal particle monitors and samplers are mainly focused on classifying and measuring supermicron particles by impactor or cyclone. Such monitors utilize the particles' inertial effect for classification and light scattering for particles detection. In these devices, particles are initially separated by inertial effects, and the particle mass collected on different stages of impactors or cyclones are measured manually after exposure. While applicable to particles with sizes larger than 0.1 μm, this existing technique is not applicable to smaller particles due to their smaller inertial effect and light scattering ability. In fact, the inertial-separation based technology is completely impractical for particles of much smaller diameters.

Existing electrical-mobility based techniques are better suited for measuring particles in the submicron and nanometer size ranges. A typical electrical-mobility-based particle sizer includes three components: a particle charger to electrically charge sampled particles to a known charge distribution, a particle-electrical-mobility-based separator to size particles and an aerosol counter to measure the concentration of sized particles.

Electrically charged aerosols are used for the size distribution measurement by the particle-electrical-mobility-based technique. The existing electrical-mobility-based technique sizes or classifies particles with diameters in the submicrometer and nanometer range. One example of a device using the electrical-mobility technique is a differential mobility analyzer (DMA). Besides the scientific instruments, attempts have also been made to implement the technique in a miniaturized aerosol classifier for the applications requiring spatially distributed measurements or monitoring particle exposure at the personal level. To retrieve real particle size distributions, sampled particles are electrically charged to well-defined charge distributions prior to an electrical-mobility-based classifier or precipitator. A miniaturized aerosol charger, providing a sufficient and stable charging efficiency, accompanies any miniaturized aerosol classifier or precipitator based on the electrical mobility technique.

Typical aerosol chargers, utilized in particle sizing instruments of electrical mobility type, are in fact neutralizers with radioactive sources such as krypton-85 ($Kr^{85}$) and polonium-210 ($Po^{210}$). In neutralizers, the radioactive sources provide bipolar ions created by the ionization of gas molecules by high energy $\alpha$ or $\beta$ particles emitted by the decay of radioactive material. Given sufficient particle residence time, particles reach stationary charge distributions in neutralizers. Prior investigations demonstrate that these bipolar ion neutralizers can measure submicron particles. There is a safety perception, however, along with regulatory provisions that complicate the usage of existing aerosol chargers. The existing aerosol chargers are not suitable for personal monitoring or spatially distributed measurements. An aerosol charger without radioactive material is lacking in the art.

Further, the charging efficiency for the existing bipolar chargers decreases with the decrease of particle size, notably in the nanometer range. To use an aerosol electrometer as a particle number counter, the low fraction of charged aerosol in the sampled particle stream demands an aerosol electrometer with a much higher sensitivity than existing aerosol electrometers. Such aerosol electrometers with higher sensitivity are expensive and bulky in size, and not suitable for low-cost, miniaturized particle sizer.

A variety of corona-discharge-based, unipolar aerosol chargers have been developed in the past decade. These existing unipolar chargers have focused on improving the charging efficiency for small particles (e.g., less than 10 nm). Without the recombination of ions of the opposite polarity, unipolar aerosol chargers generally provide better charging efficiency than bipolar chargers. The loss of charged particles due to electrostatic and/or space charge effects is, however, often severe in existing aerosol chargers. As examples, techniques implementing alternating current electrical fields and/or sheath air are utilized in the existing unipolar chargers to reduce charged particle losses. These enhancement features increase the operational complexity, and are therefore unsuitable for a low-cost, miniature device. No existing corona-discharge-based, unipolar aerosol charger provides simple operation and compactness while preserving sufficient and stable charging efficiency.

Among different types of electrical mobility analyzer designs, the simplest one is the precipitation type (e.g., cylindrical or disk configurations). In an electrical precipitator of cylindrical configuration, an electrical field is established in the annular aerosol flow channel, constructed by an outer cylinder and inner rod. Particles are electrically charged prior to being introduced into the annular flow channel. The performance of a precipitator is characterized by the penetration efficiency as a function of applied voltage at a fixed aerosol flowrate. A critical electrical mobility, $Z_{pc}$, for any given voltage may then be determined from the penetration curves. Charged particles having electrical mobility larger than $Z_{pc}$ are completely precipitated by a given voltage. Particle size distribution may be obtained by stepping the precipitation voltage through the entire voltage range and measuring the electrical charges associated with penetrating particles. A disk-type electrostatic aerosol precipitator includes a central metal disk sandwiched between two parallel metal disk electrodes. Electrically insulating spacers create two flow chambers between the middle and top/bottom disks. An electrically charged aerosol flow is introduced into the top flow chamber by a straight tube connected to the centre of the top disk, and flows radially outwards. By creating an electrical field across the flow chamber, particles with sufficient electrical mobilities are removed from the aerosol stream. The outflow is directed to the flow chamber between the middle and bottom disks through an annular slot. In this bottom flow chamber, the aerosol flow moves inward and converges to an exit tube connected to the center of the bottom disk. In some existing systems, no electrical field is established in the bottom flow chamber since it is used for aerosol transport only. However, such existing devices are too large for some applications. For example, while the thickness of the flow chambers is 2 mm in some existing systems, a typical diameter for an existing device is about 8 in (203.2 mm). Miniaturized electrical mobility analyzers are lacking in the art.

FIG. 1 is a schematic diagram of an embodiment of the invention as described herein. The figures illustrate exemplary embodiments of the invention, but other embodiments are within the scope of the invention. The mini-electrostatic sizer described herein includes one or more of the following components: a unipolar mini-charger, a disk precipitator, and a miniaturized aerosol electrometer. In an embodiment (not shown), a power supply is connected to the mini-charger and to the disk precipitator. Further, a pump may be attached to the output of the electrometer.

Figure 2:
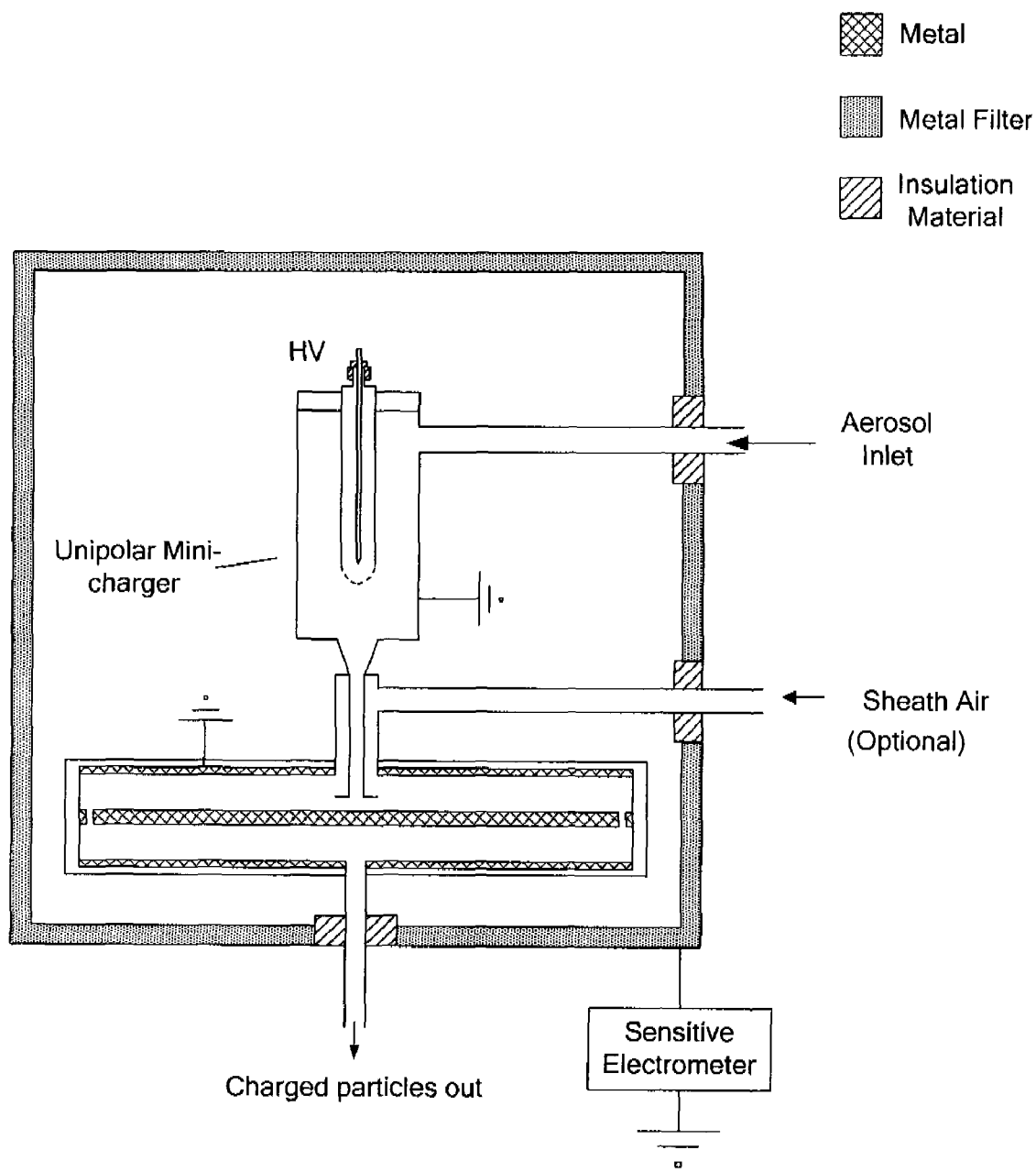
FIG. 2 is a schematic diagram of an alternative embodiment of a mini-nanoparticle sizer in accordance with the current invention.

FIG. 2 is a schematic diagram of an alternative embodiment of the invention as described herein. The embodiment shown in FIG. 2 does not include a filter (e.g., the electrometer) to trap particles within the aerosol electrometer.

In an example embodiment of the unipolar mini-charger, a corona tip is placed in the center point of a semi-spherical metal mesh. When a certain high positive voltage is applied on the corona tip with the semi-spherical metal mesh grounded, a corona is triggered between the corona tip and the metal mesh, and a lot of positive ions are generated. A small negative voltage is applied to the charger body so that the positive ions produced are driven out through the semi-spherical metal mesh by electrical field between the metal mesh and the charger body. The ions then mix with the particles passing through the charger. Unipolar charging takes place and the particles become charged. The charger, further described below, prevents aerosol flow from passing the corona zone, allowing the corona tip to be free from contaminated by the particles. Moreover, the compact design leads to a small charging zone that reduces the charged particle loss. Further, the smaller corona tip in this design enables use of a lower voltage to trigger the corona. In some embodiments, the mini-charger may be run in a reverse aerosol flow direction.

In the disk precipitator, the metal disk is placed in the middle of the device, and high voltage is applied through a high voltage cable. The disk is in round shape and has a size approximately identically to a U.S. dime coin. The disk includes a series of small orifices close to the outer circumference through which the aerosol flows. The upper and lower metal plates may be grounded or connected to high voltage, and an electrical field is created between the grounded plate and the disk when voltage is applied on the disk. The aerosol from the inlet tube diverges in the direction of the disk radius, passes through the orifices, and converges in the direction of the disk radius to the outlet tube.

When a certain voltage is applied on the metal disk, the charged particles introduced into the precipitator are deflected by the electric field. Particles with a sufficiently high electrical mobility are precipitated, while those with lower mobility escape collection and exit the precipitator and are detected by the aerosol electrometer downstream.

FIG. 2 also shows that a sheath air is added into the disk precipitator to improve the sizing resolution. The elimination of the sheath air lowers the operational complexity with the sacrifice on the sizing resolution. Regardless of whether sheath air is used, the mini-classifier may be operated using either one or two sides of the disk. In the exemplary embodiment, the mini-classifier is operated using both sides of the disk. The two-sided design and operation enables use of a lower voltage to remove the same amount of charged particles as compared with a single-side design. Moreover, the disk design makes it possible to stack multiple disks into one package while maintaining its compact configuration.

The concentration of charged particle exiting from the disk classifier described above is then detected by an aerosol Faraday cage electrometer. The electrometer uses a metal porous media as a filter to trap all the charged particles fed in the meter. The electrical current generated by the charged particles depositing on the metal filter is measured by an electrometer. The electrical current is then inverted back to the particle number concentration with a known charge distribution of the particles. Rather than measuring induced electrical current, as is done by the conventional aerosol electrometer, the use of metal porous filter enables the electrometer to measure the direct electrical current, thereby improving the response and sensitivity of small current measurement. Moreover, the size of the metal filter is designed to be larger than that of aerosol inlet tube to reduce the dead volume, further improving the response of small current measurement. The porous media also ensures all the charged particles are trapped once passing through the filter. In addition, because the design detects the direct current instead of induced current, the outer electrometer housing is slightly larger size than that of the metal filter. The arrangement keeps the meter compact and leads to a fast response to the change of electrical current.

The mini-aerosol corona charger (MACC) is a technology for electrically charging aerosol particulates. This capability is of direct applicability to the measurement of particle electrical mobilities. Because a particle's electrical mobility expresses the ratio of viscous to electrostatic forces that it experiences, the ability to impose well characterized charge states enables the ability to measure particle size distributions. This technology applies to the measurement of particles in the submicron size range. Relative to existing technologies, the geometry, construction, and method of operation of the mini-charger allows operation at a low applied voltage, provides an extremely compact device, affords excellent charge efficiency and low internal losses.

FIG. 3 shows a schematic diagram of an example mini-charger that may be used with the apparatus shown in FIGS. 1 and 2. The mini-charger has a length of approximately 1.0 inch and a diameter of approximately 0.5 inch. The simple construction of the mini-charger includes an outer metal tube case with the aerosol outlet at one end, and a corona discharge module for unipolar ion production inserted from the other end and electrically insulated from it. The corona module is a metal tube of smaller diameter, with one end micro-machined to form a cap with a perforated spherical dome. The cap was designed to maximize its open area, which constitutes approximately 74% of its total surface. A pointed solid tungsten needle is coaxially aligned with and electrically insulated from the module tube. The tip of the corona needle was machined to an extremely fine radius using micro-EDM (Electron Discharge Machining), and is positioned at the center of the perforated dome. By applying a high voltage on the tungsten needle with respect to the surrounding metal tube, high electrical field intensity is established around the needle tip. For the operation of this module, a high positive voltage was applied to the tungsten needle and a low positive voltage to the module case. If the electrical field strength at the needle tip is sufficiently high, air molecules around the tip are ionized and corona discharge is thus initiated. Ions produced by the corona discharge module are then transported through the perforated dome by establishing a small electrical potential between the dome and charger case (i.e., ion-transport voltage). The field was created by electrically grounding the charger case since the low voltage was applied at the corona module case. The particle charging zone, where particles mix with ions, is formed by the space between the perforated dome and the exit portion of charger tube case. The charging zone arrangement in the mini-charger allows particles to quickly exit once they are electrically charged, thus reducing the loss of charged particles. The charging zone design is different from those in all other unipolar aerosol chargers, in which the charging zones are located well inside the devices.

The simple design and compact size make the mini-charger well suited for use with portable aerosol sizing instruments based on a particle electrical mobility technique. The extrinsic charging efficiency of the mini-charger was first optimized for two different aerosol flowrates, (i.e., 0.3 and 1.5 lpm). Alternative embodiments allow different flowrates. Additionally, alternative embodiments also include flowrates between approximately 0.3 lpm and approximately 1.5 lpm. In an embodiment, the optimal settings for the operation are a corona current of approximately 1 µA and an ion-driven voltage of approximately 40 V for the 0.3 lpm flowrate, and approximately 2 µA and approximately 120 V for the 1.5 lpm flowrate. Alternative embodiments may vary the current and voltage used to generate the flowrate. Both intrinsic and extrinsic charging efficiencies of the mini-charger at the optimal operational conditions are evaluated for particles in the diameters ranging from 10 to 200 nm. As an example, the intrinsic charging efficiency of the mini-charger reaches 100% at 20 nm for the 0.3 lpm flowrate, and at 45 nm for the 1.5 lpm flowrate. The higher intrinsic charging efficiency at the low flowrate is due to the longer residence time of particles in the device. The extrinsic charging efficiency, however, is higher for the 1.5 lpm flowrate than for the 0.3 lpm flowrate due to the charged particle loss in the mini-charger. Charge distributions of test monodisperse particles of different sizes were also measured by the Tandem-DMA technique.

The body of the exemplary mini-charger includes a sealed, conductive outer shell that provides a reference potential, and establishes the geometry of the aerosol flow through the charging region. The aerosol flow containing entrained particles enters the outer shell via a tangential inlet tube, is directed towards the charging region, and exits via an axially oriented outlet tube. The conductive outer shell establishes a reference potential, in part through the inclusion of electrical insulators that isolate the outer case.

The mini-charger utilizes a corona discharge to impose a well characterized, unipolar electrical charge distribution on submicron aerosol particles. A corona discharge assembly is electrically isolated from and coaxially located within the outer shell. The corona discharge assembly includes an inner needle electrode whose tip has been machined to a radius of extremely small dimensions. The tip of this coaxially located within an outer tube, biased at a suitable electrical potential to establish corona discharge. One end of the outer corona tube is machined to form a hemispherical, permeable cap. The tip of the needle electrode is placed at the radius of curvature of the hemispherical surface. A biased potential established between the corona tube and the outer case induces the flow of ions generated by the discharge to penetrate the permeable hemispherical surface and enter the charging region. Electrical insulators isolate the inner corona tube and the discharge needle. The radii of the electrode and hemispherical cap are optimized to minimize the discharge voltage, to increase the useable lifetime of the device, and to minimize the dependence of the operational characteristics on manufacturing tolerances.

During operation, the particles of interest are entrained in an aerosol flow. A sample of this flow enters the mini-charger through a tangentially oriented inlet tube. The resulting cyclonic flow established by the geometry of the outer case, inner corona tube, and tangential inlet tube insures uniform mixing of the aerosol inside the mini-charger. The location of the permeable, hemispherical end cap of the inner corona tube proximate to the axial outlet tube minimizes internal particle losses. The establishment of an electrical potential between the outer case and the inner corona tube results in the passage of ions generated by the discharge to exit the permeable cap of the corona tube and enter the charging region. The establishment of a suitable electrical potential between the discharge needle and inner corona tube induces a controlled corona discharge. The flow passes through permeations in the separating barrier before entering the second control chamber. In some embodiments, the aerosol flow may be in a reverse direction, such that the aerosol flow exits the mini-charger through the inlet tube.

Figure 4:
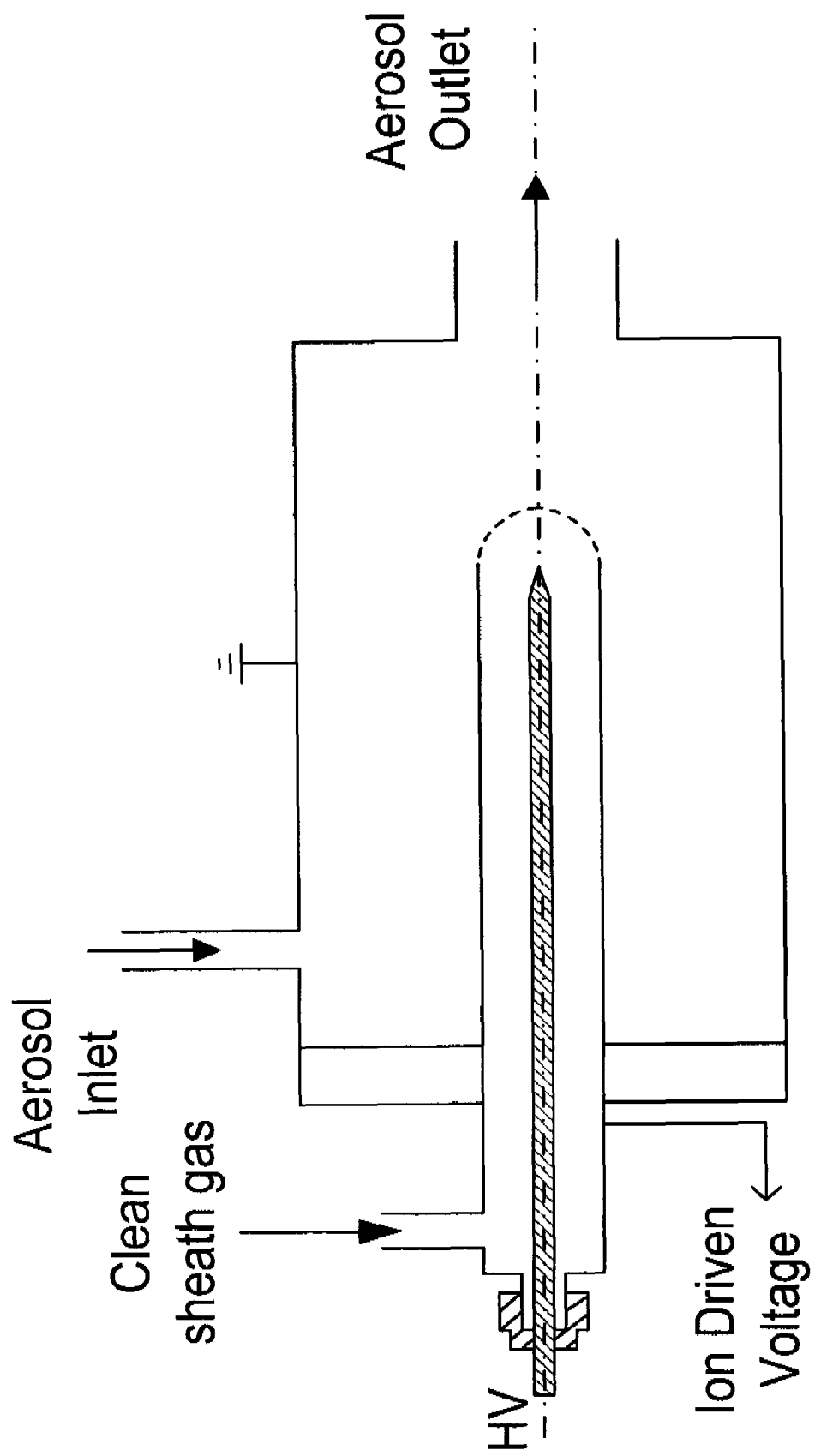
FIG. 4 is a schematic diagram of an alternative embodiment of a mini-charger that may be used with the mini-nanoparticle sizers shown in FIGS. 1 and 2.
Figure 5:
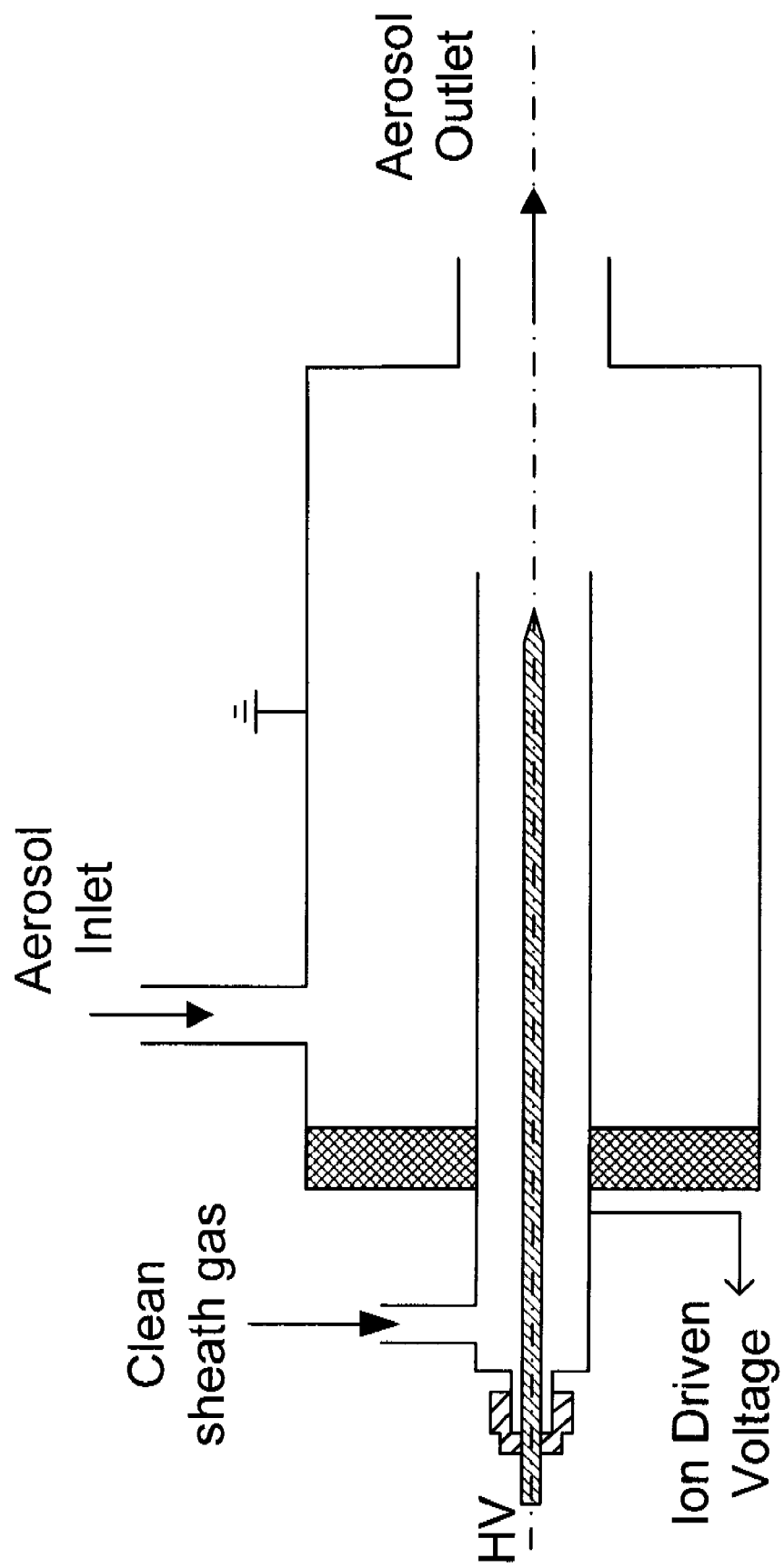
FIG. 5 is a schematic diagram of another alternative embodiment of a mini-charger that may be used with the mini-nanoparticle sizers shown in FIGS. 1 and 2.
Figure 6:
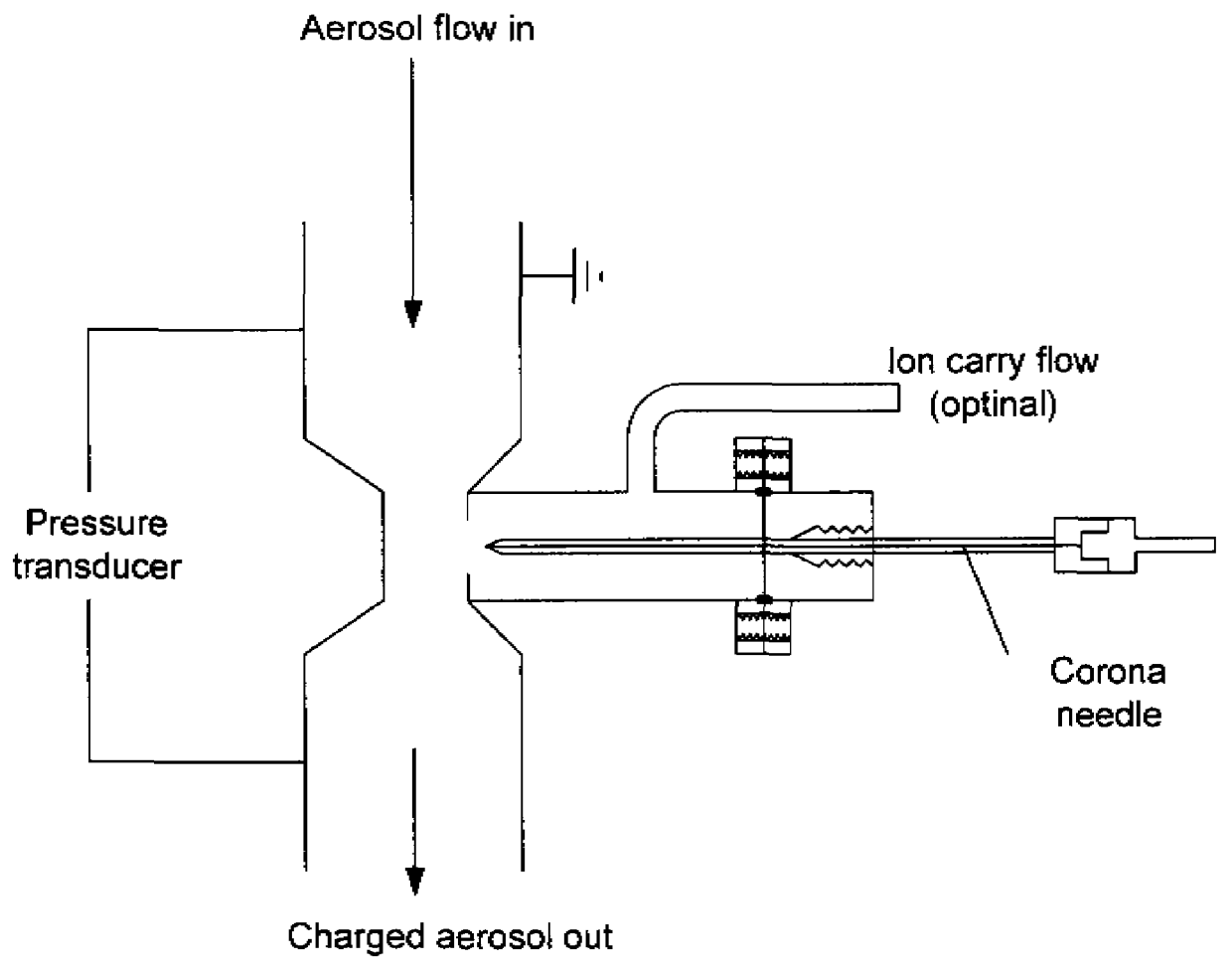

In an embodiment, as shown in FIG. 4, the mini-charger includes a conduit for adding clean sheath gas to the aerosol. Inclusion of a clean sheath gas prevents aerosol from forming deposits on the corona discharge wire and tip, thereby prolonging the lifetime of the corona needle. The clean sheath gas may be different from the aerosol carrier gas, allowing the mini-charger to produce ions with different molecular weights. The aerosol charging efficiency may be further increased if ions of smaller molecules, as compared with aerosol carrier, were produced. Using a clean sheath gas also minimizes the effects of environmental factors on the corona operation, such as temperature, pressure, and/or relative humidity. FIG. 5 shows an alternative embodiment that may further reduce the manufacturing cost associated with the mini-charger, wherein the mini-charger does not include a hemispherical cap covering the electrode tip. The aerosol flow is directed into the mini-charger by the inlet tube, which is connected at approximately a 90° angle to the charger tube case, near the corona discharge module. The annular spacing between the charger and module cases allows the aerosol flow to be uniformly distributed in the circumferential direction before it mixes with ions. The design minimizes the possibility of particles entering the corona module and contaminating the tip, and thus prolongs the lifetime of the needle while keeping the charger construction simple. FIG. 6 shows another alternative embodiment of a mini-charger that may be used with the mini-nanoparticle sizers shown in FIGS. 1 and 2. The mini-charger shown in FIG. 6 includes an aerosol flow channel having a contraction-and-expansion section, and a corona discharge tube chamber having an option of introducing ion carry flow. The corona discharge tube chamber is installed at the reduced-area section of the aerosol flow channel. Moreover, an orifice plate is used to separate the aerosol flow channel and corona chamber. Either positive or negative ions can be produced in the corona chamber. The reduced-area section design arranges the aerosols to flow in the region close to the orifice opening, thus mixing with ions produced in the corona chamber. Aerosol is thus electrically charged in the charger. One advantage of this charger is that no bias voltage is needed to channel ions into the aerosol flow, although the inclusion of ion-bias voltage may improve the charger performance. Another advantage of this charger design is that one can use the pressure drop across the reduced-area section to monitor the aerosol flow through the channel. The ion carry flow feature is an option for this charger. The feature channels more ions into the aerosol flow channel and thus enhances the charging efficiency of this charger.

Characterization of the performance of the mini-charger may comprise: i) measurements of the charging efficiency, and ii) measurements of the charge-state distribution. The measurements were carried out with the experimental setup shown in FIG. 7. Polydisperse particles with a mean diameter less than 50 nm were generated by the evaporation-condensation technique. Bulk material of the test particles was loaded in a combustion boat and placed in a high temperature tube furnace. A vapor-rich stream was produced by passing inert gas through the furnace tube. Polydisperse nanoparticles were formed by quenching the hot vapor-rich stream with particle-free, inert gas at room temperature. For test particles with mean diameters ranging from approximately 50 to 200 nm, polydisperse particles were generated by a home-made collision atomizer with solutions of particle material at different volumetric concentrations. Downstream of the particle generation systems, a Nano-Differential Mobility Analyzer (Nano-DMA), such as a model 3085 DMA commercially available from TSI Incorporated, was used to classify monodisperse particles of diameters less than 50 nm, and a standard DMA, such as a model 3081 DMA commercially available from TSI Incorporated, was used to classify particles of diameters in the range of 50-200 nm. Since the particles exiting from the DMAs are electrically charged, a $Po^{210}$ neutralizer and a charged particle remover were used downstream of the DMAs to obtain neutral test particles. An optional flow bypass was also included in the setup for penetration measurement of singly charged particles through the mini-charger.

For the charging efficiency measurements, the charged fraction of particles after passing through the mini-charger was determined. This was accomplished by installing a second charged particle remover at the downstream of the mini-charger to remove the charged fraction of particles from the aerosol flow, and an ultrafine condensation particle counter (UCPC), such as a model 3025A UCPC commercially available from TSI Incorporated, to measure the number concentration of neutral particles in the flow after passing through the second charged particle remover. For the charge distribution measurements, the particles leaving the mini-charger were directly introduced into a Scanning Mobility Particle Sizer (SMPS), such as a model 3080 SMPS commercially available from TSI Incorporated, without the $Kr^{85}$ neutralizer installed. Depending on the test particle sizes, a Nano-DMA or a standard DMA was used in the SMPS. The SMPS scanned the electrical mobility distribution of particles exiting the mini-charger, from which the particle charge distribution was inferred.

In all the measurements, the aerosol flowrate through the mini-charger was controlled by the pump in the UCPC. Both low and high flowrate modes of the UCPC (i.e., 0.3 and 1.5 lpm) were used.

Both the intrinsic and extrinsic charging efficiencies were measured in this study. The extrinsic charging efficiency includes the particle loss during the charging and transportation processes, but intrinsic efficiency does not.

In this experiment the intrinsic charging efficiency was measured using a known method, and defined as:

$$\eta_{in} = 1 - \frac{N_1}{N_2} \quad (1)$$

where $\eta_{in}$ is the intrinsic charging efficiency and $N_1$ is the particle number concentration measured downstream of the second charged particle remover with both the corona discharge module and the second charged particle remover on. $N_2$ is measured in similarity to $N_1$ but with both the corona and second charged particle remover off.

The extrinsic charging efficiency was evaluated a known method, and described as:

$$\eta_{ex} = \frac{N_3 - N_1/P_{cpr}}{N_4} \quad (2)$$

where $\eta_{ex}$ is the extrinsic charging efficiency, $N_3$ is the number concentration of particles exiting the mini-charger, $N_4$ is the number concentration of particles entering the charger and $P_{cpr}$ is the penetration of neutral particles through the second charged particle remover.

Figure 7:
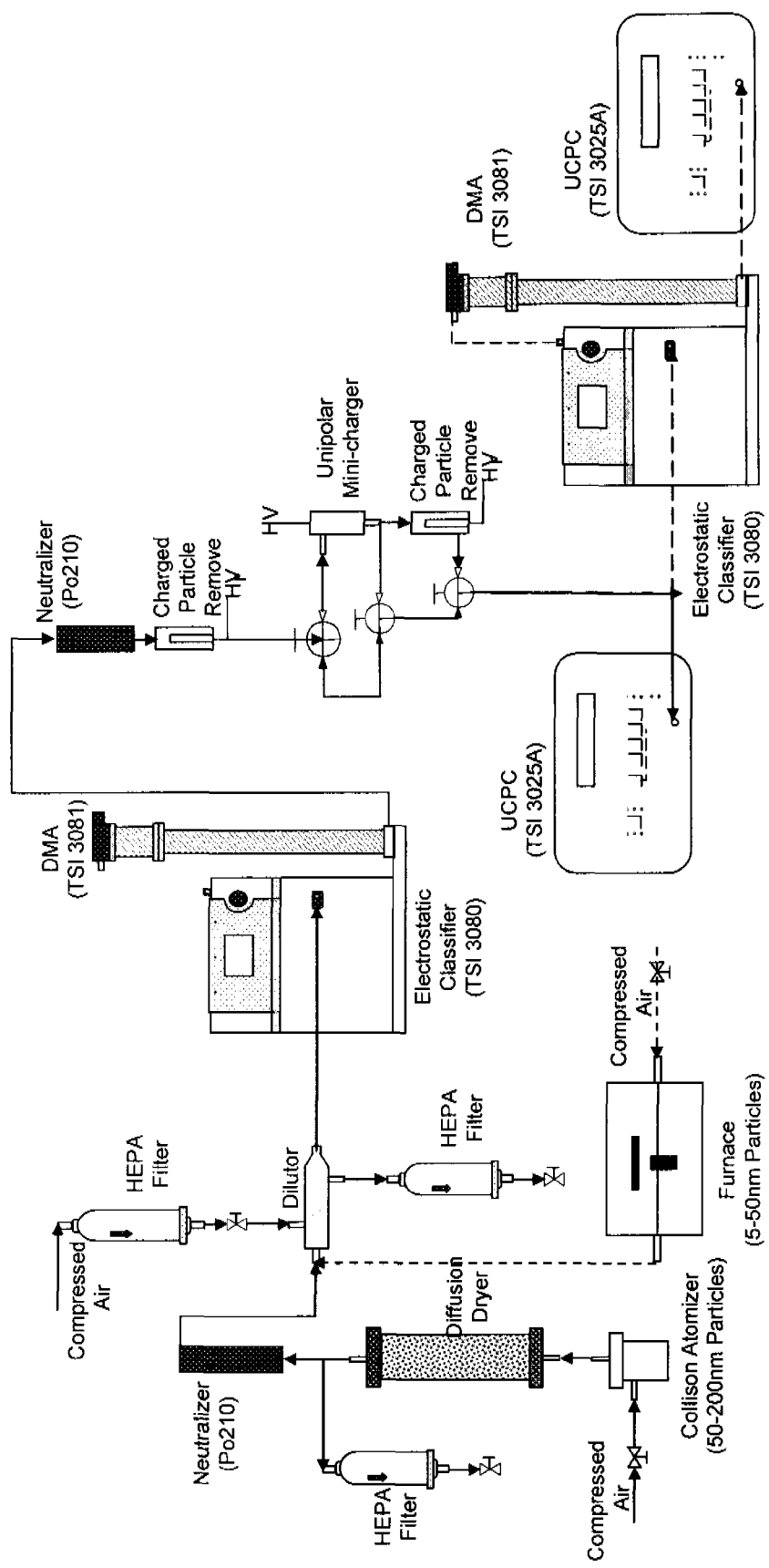
FIG. 7 is a schematic diagram of an experimental setup for a performance evaluation of the mini-chargers shown in FIGS. 3-6.

The tandem DMA technique was used to measure the particle charge distribution of monodisperse test particles at different sizes. As shown in FIG. 7, the electrical mobility distribution of particles leaving the mini-charger was directly measured by a scanning mobility particle sizer (SMPS) without the $Kr^{85}$ particle neutralizer installed. Since the test particles entering the mini-charger are monodisperse in size, the electrical mobility distribution of the particles, as measured by the SMPS, indicates the charge distribution of the test particles after passing through the mini-charger. The information about the charge distribution of the particles is used to recover the size distribution of particles to be characterized.

Note that the charge distribution measured by this method characterizes the extrinsic, not intrinsic performance of the mini-charger, therefore this set of distribution data should not be directly compared with that predicted by the particle charging modeling. Monodisperse particles having different number of electrical charges result in particles of different electrical mobility, which exhibit different penetration through the mini-charger. It is difficult to experimentally evaluate the penetration of multiply charged particles through the device, especially during the charging process. Without the charged particle penetration data, it is impossible to derive the intrinsic charge distribution in the charging zone. However, the extrinsic charge distributions for particles of different sizes are used in the data reduction process for the application of the particle size measurement.

The optimization of operational settings maximizes the performance of an aerosol charger. Practical applications gain the most benefit if the optimization focuses on the extrinsic charging efficiency. For an aerosol charger based on the ion attachment technique, the intrinsic charging efficiency of the device is affected mainly by the so-called $N_i t$ value (where $N_i$ is the ion concentration, and t is the particle residence time in the charging zone). This situation exists when the charging mechanism is dominated by ion diffusion, as is the case when charging particles in the submicron and nanometer range. For the mini-charger, the particle residence time may be controlled by adjusting the aerosol flowrate. The ion concentration in the charging zone may be controlled by either the corona current or ion-transport voltage. With a higher corona current or higher ion-transport voltage, the ion concentration in the charging zone of the mini-charger may be increased, leading to an increase in the intrinsic charging efficiency. However, the increase of the ion concentration results in more charged particle loss, because of the increased space charge effect and/or more electrostatic precipitation by the increased ion-transport voltage. Thus, the extrinsic charging efficiency of the mini-charger may not be further increased by simply increasing the ion concentration in the charging zone.

Figure 8:
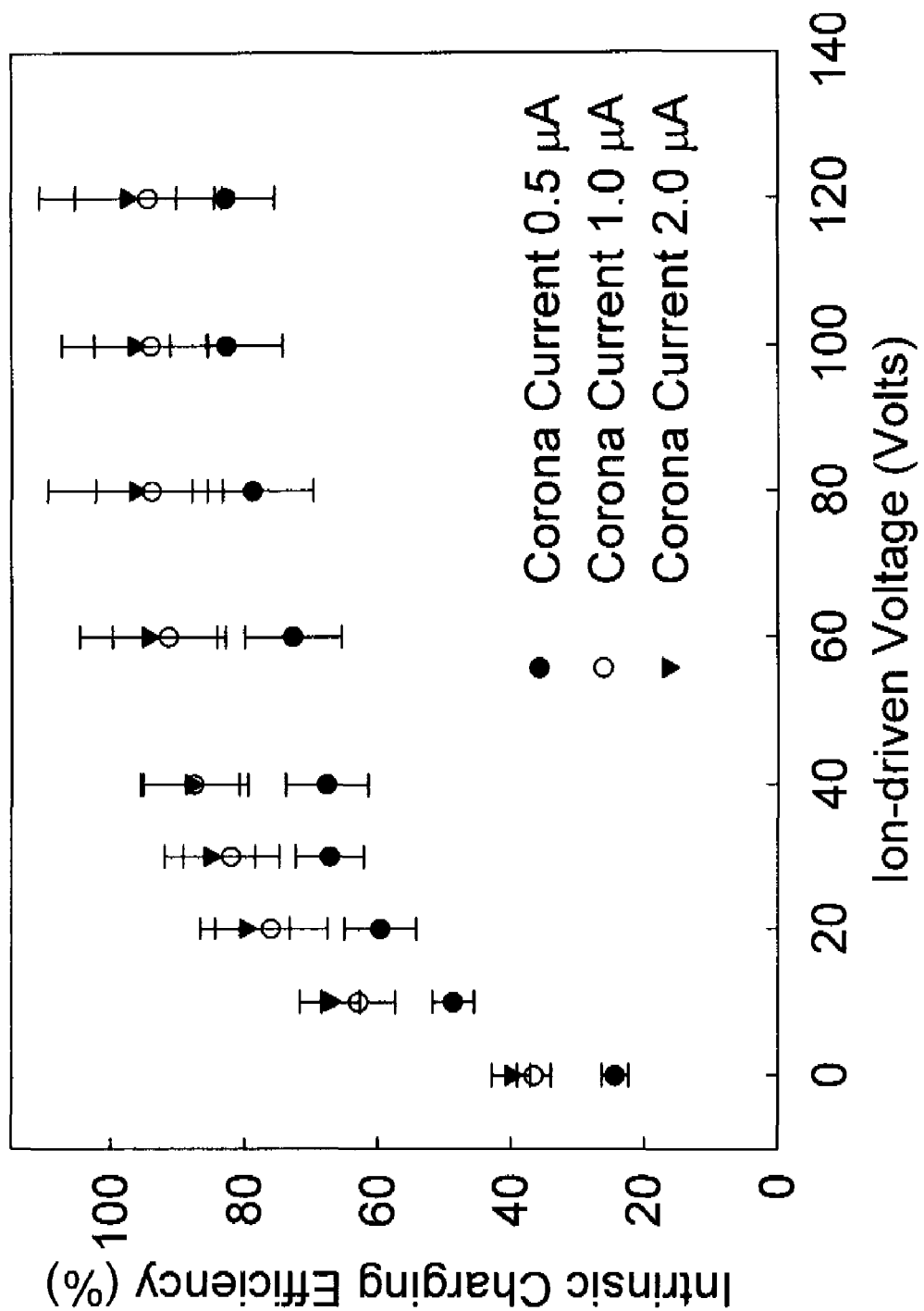
FIG. 8 is a graph illustrating the intrinsic charging efficiency of 20 nm diameter particles under different corona current and ion-transport voltages using the mini-chargers shown in FIGS. 3-6 and the experimental setup shown in FIG. 7.
Figure 9:
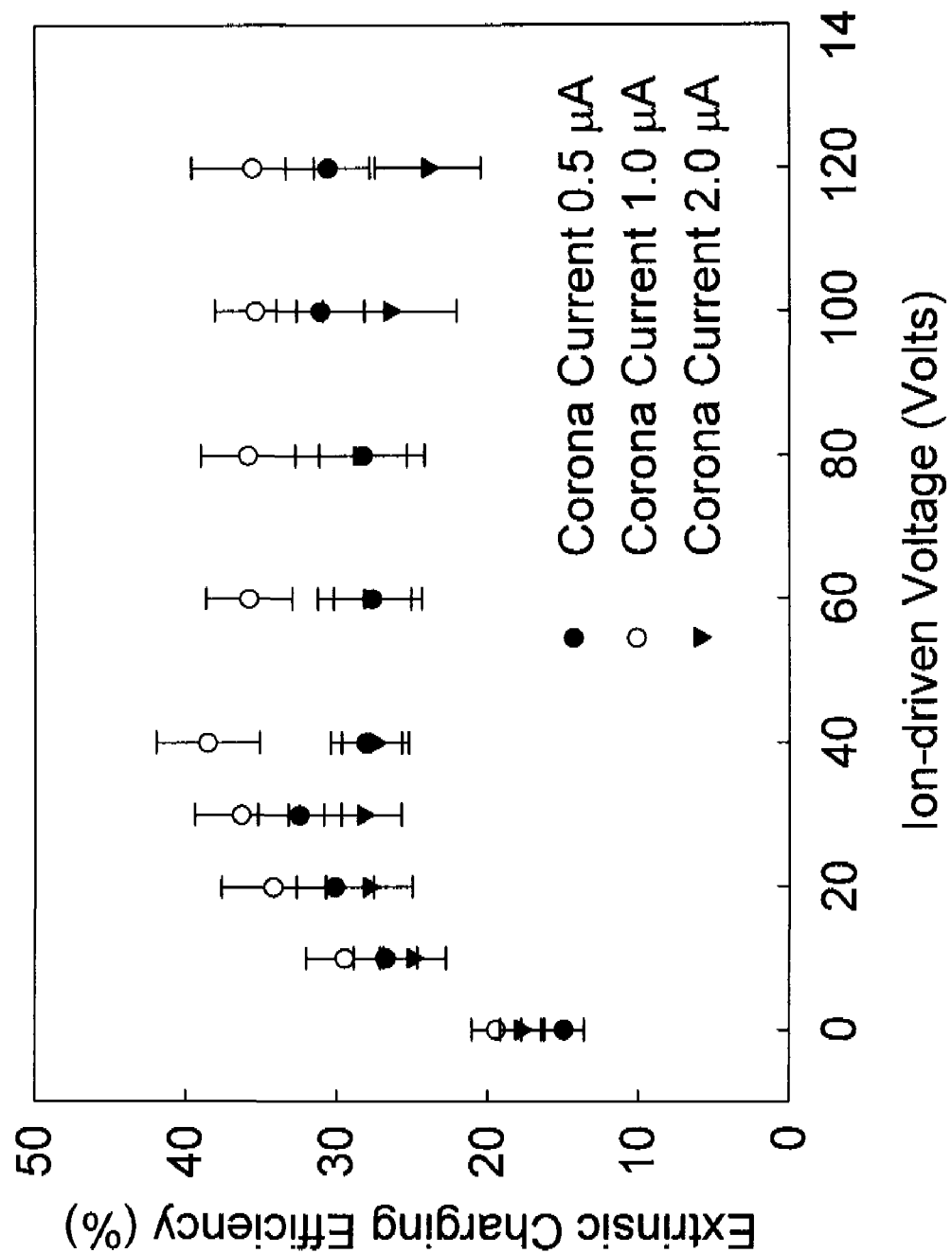
FIG. 9 is a graph illustrating the extrinsic charging efficiency of 20 nm diameter particles under different corona currents and ion-transport voltages using the mini-charger shown in FIGS. 3-6 and the experimental setup shown in FIG. 7.

Twenty nanometer (20 nm) monodispere particles were utilized as a test aerosol in an embodiment. FIGS. 8 and 9 show the intrinsic and extrinsic charging efficiencies of the mini-charger at different corona discharge currents and ion-transport voltages, respectively. The aerosol flowrate was fixed at 0.3 lpm. It is evident from FIG. 8 that the intrinsic charging efficiency increases with an increase in the ion-transport voltage and/or corona current. Nearly 100% intrinsic charging efficiency was achieved with a corona current of 2 µA and an ion-transport voltage of 120V. The result in FIG. 9, however, shows that the maximal extrinsic charging efficiency was achieved at a corona current of 1.0 µA and an ion-transport voltage of 40 V. This setting was thus used for the mini-charger for the aerosol flowrate of 0.3 lpm. A similar optimization procedure was followed for the 1.5 lpm aerosol flowrate, and was found that the maximal extrinsic charging efficiency occurred at a corona current of 2.0 µA and an ion-transport voltage of 120 V.

Figure 10:
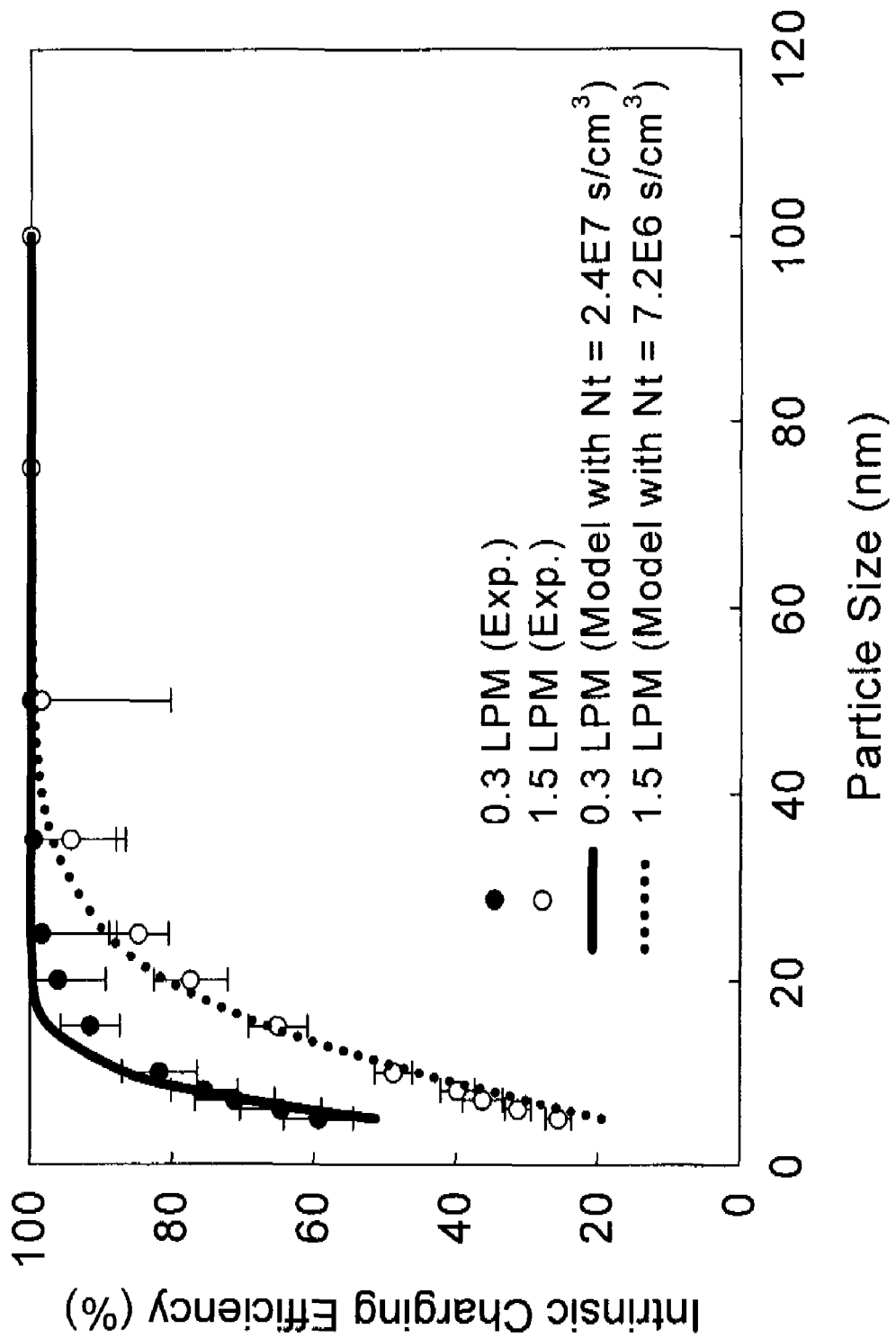
FIG. 10 is a graph illustrating the intrinsic charging efficiency of the mini-charger shown in FIGS. 3-6 as a function of particle size.

The intrinsic charging efficiency of the mini-charger at aerosol flowrates of 0.3 and 1.5 lpm is shown in FIG. 10. The corona currents and the ion-transport voltages corresponding to two test aerosol flowrates obtained in the previous optimization experiment were used for this measurement. For the aerosol flowrate of 0.3 lpm, the intrinsic charging efficiency is higher than 80% for particles with diameters larger than 10 nm. At 5 nm particle size, the efficiency remains 60%. For the aerosol flowrate of 1.5 lpm, charging efficiency higher than 80% occurs at particle sizes larger than 20 nm. In general the intrinsic charging efficiency is higher for the case of 0.3 lpm than for the case of 1.5 lpm, because of the longer residence time of particles in the charging zone.

Also included in FIG. 10 are curves calculated by the stochastic birth-and-death particle charging models with the ion-particle combination coefficient estimated by the Fuchs limiting sphere model. The electrical mobility and ionic weight for the positive ions used in the calculation are 1.33 $cm^2/Vs$ and 200 amu, respectively. The $N_i t$ value listed for each flowrate was obtained from the best fit to the experimental data. The particle charging model assumes that the ion concentration in the charging zone is spatially uniform and constant. The difference between the experimental and calculated data may be due to the spatial non-uniformity of the ion concentration in the charging zone of the mini-charger.

Figure 11:
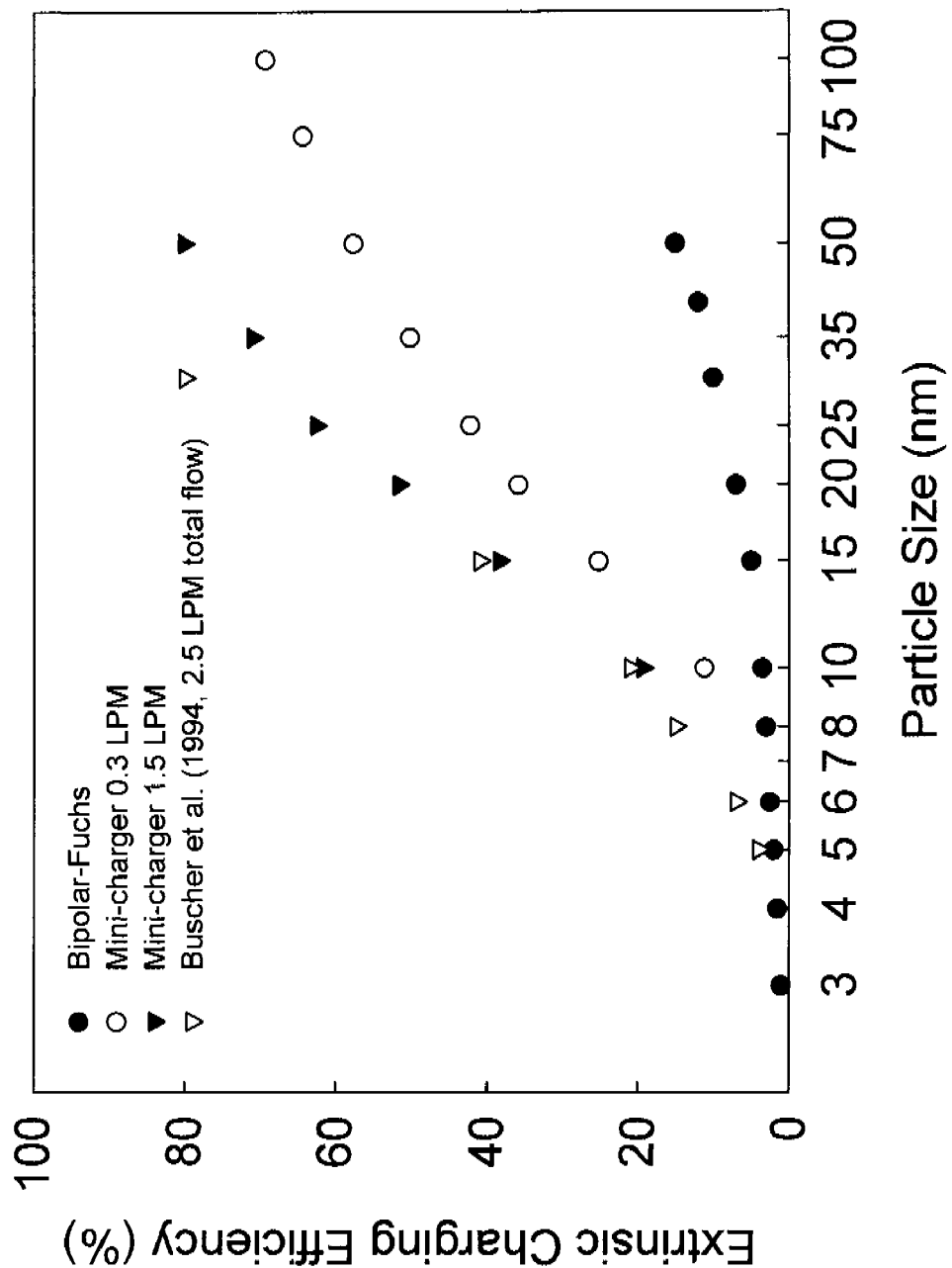
FIG. 11 is a graph illustrating a comparison of the extrinsic charging efficiency of the unipolar mini-charger shown in FIG. 3-6 with that of bipolar charging.

The measurement of the extrinsic charging efficiency of the mini-charger accounts for losses resulting from the space charge effect and/or electrostatic precipitation. The extrinsic charging efficiency is also used in the data-reduction scheme to recover the size distribution of particles to be characterized. FIG. 11 shows the extrinsic charging efficiency for different particle sizes at 0.3 and 1.5 lpm aerosol flowrates. For comparison, the bipolar ion charging efficiency as a function of particle size is also shown. The bipolar ion charging data were calculated by the same birth-and-death particle charging model used to predict the intrinsic charging efficiency, except for consideration of the presence of bipolar ions. Also included in the same figure is the experimental extrinsic charging efficiency of the unipolar aerosol charger.

The comparison with the bipolar ion charging data demonstrates improved extrinsic charging efficiency for particles larger than 10 nm, at both 0.3 and 1.5 lpm aerosol flowrates. Although the intrinsic charging efficiency for the aerosol flowrate of 1.5 lpm is less than that of 0.3 lpm (shown in FIG. 10), FIG. 11 shows that better extrinsic charging efficiency was achieved at the aerosol flowrate of 1.5 lpm, where the shorter particle residence time in the charging zone leads to less charged particle loss. Thus, the lower intrinsic charging efficiency for the 1.5 lpm flowrate case is compensated by the reduced charged particle losses. It is also noted that the extrinsic charging efficiency of the mini-charger operated 1.5 lpm is comparable with that of the unipolar charger, wherein the AC electrical field and sheath air features are implemented to reduce the charged particle loss. The unipolar mini-charger thus provides comparable charging efficiency for particles in the submicron and nanoparticle range, while keeping its compact design and simple operation.

The issue of multiple charges on particles, especially for particles in the larger submicron size range, becomes a concern from the overall measurement perspective. Multiple charging complicates the data reduction scheme used to recover the size distribution. In this experiment, the charge distributions of monodisperse test particles at differing sizes were measured.

Figure 12:
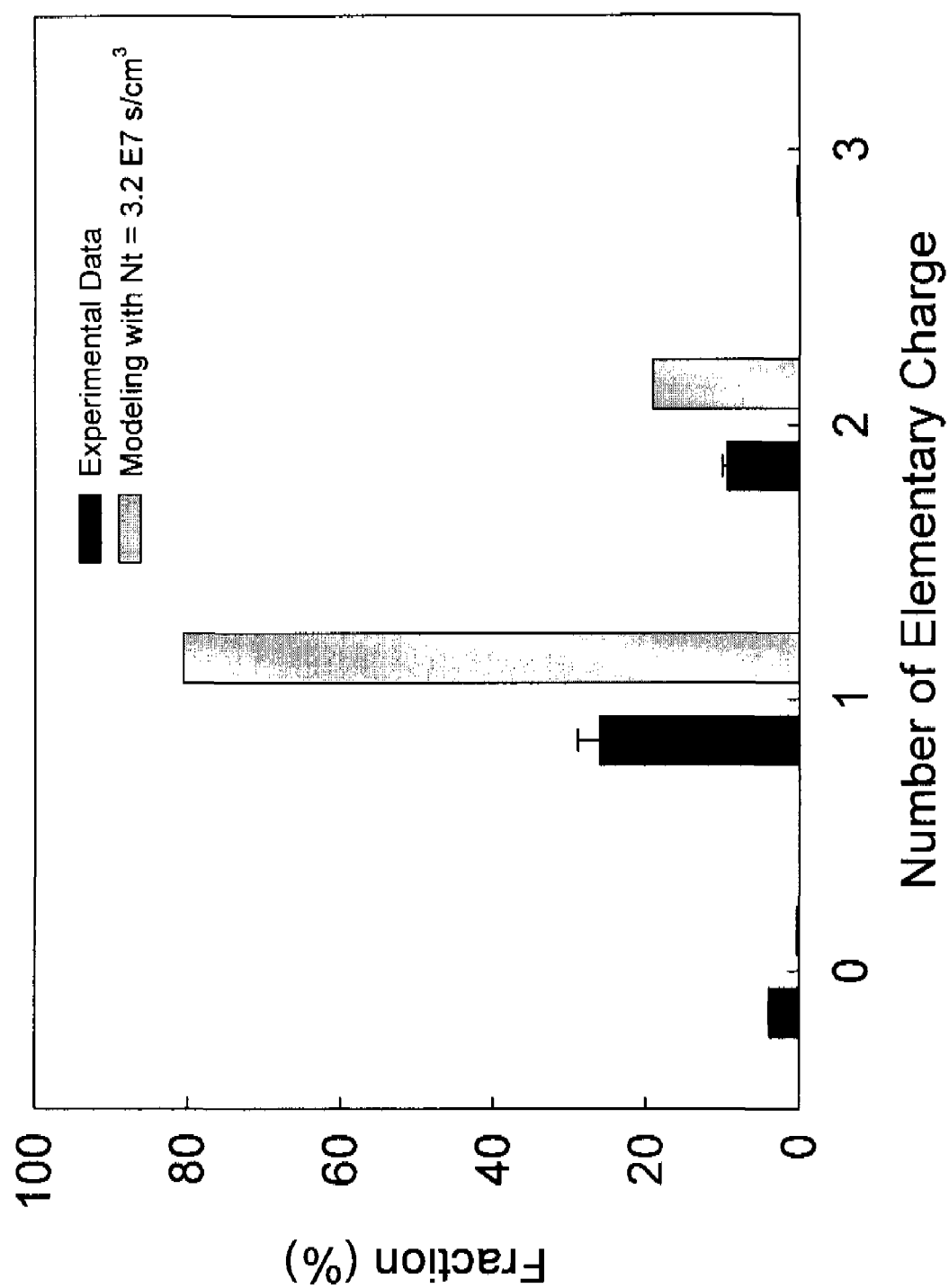
FIG. 12 is a graph illustrating the charge distributions of monodisperse test particles after passing through the unipolar mini-charger shown in FIGS. 3-6, with 20 nm diameter particles and a 0.3 lpm flowrate.
Figure 13:
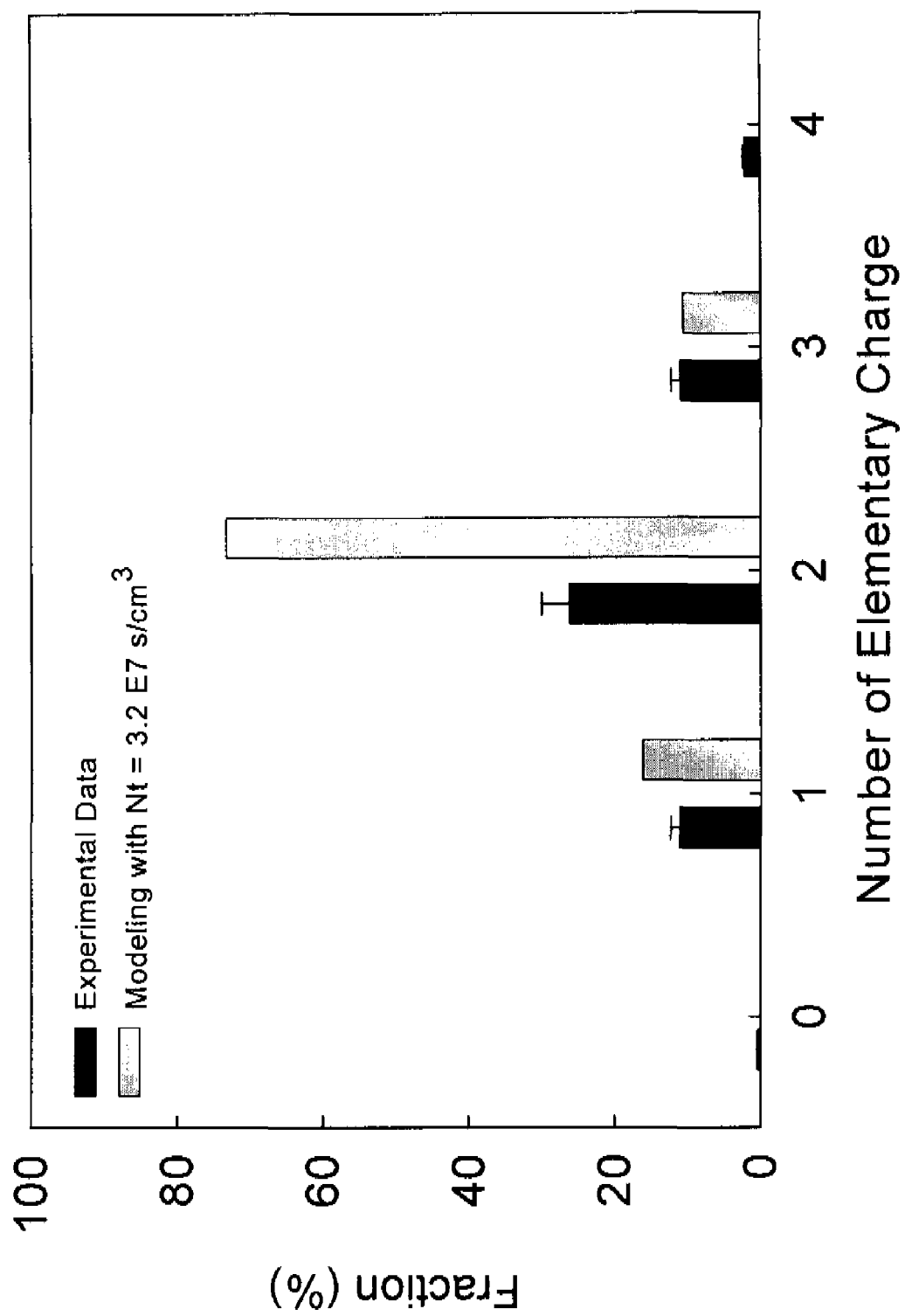
FIG. 13 is a graph illustrating the charge distributions of monodisperse test particles after passing through the unipolar mini-charger shown in FIGS. 3-6, with 35 nm diameter particles and a 0.3 lpm flowrate.
Figure 14:
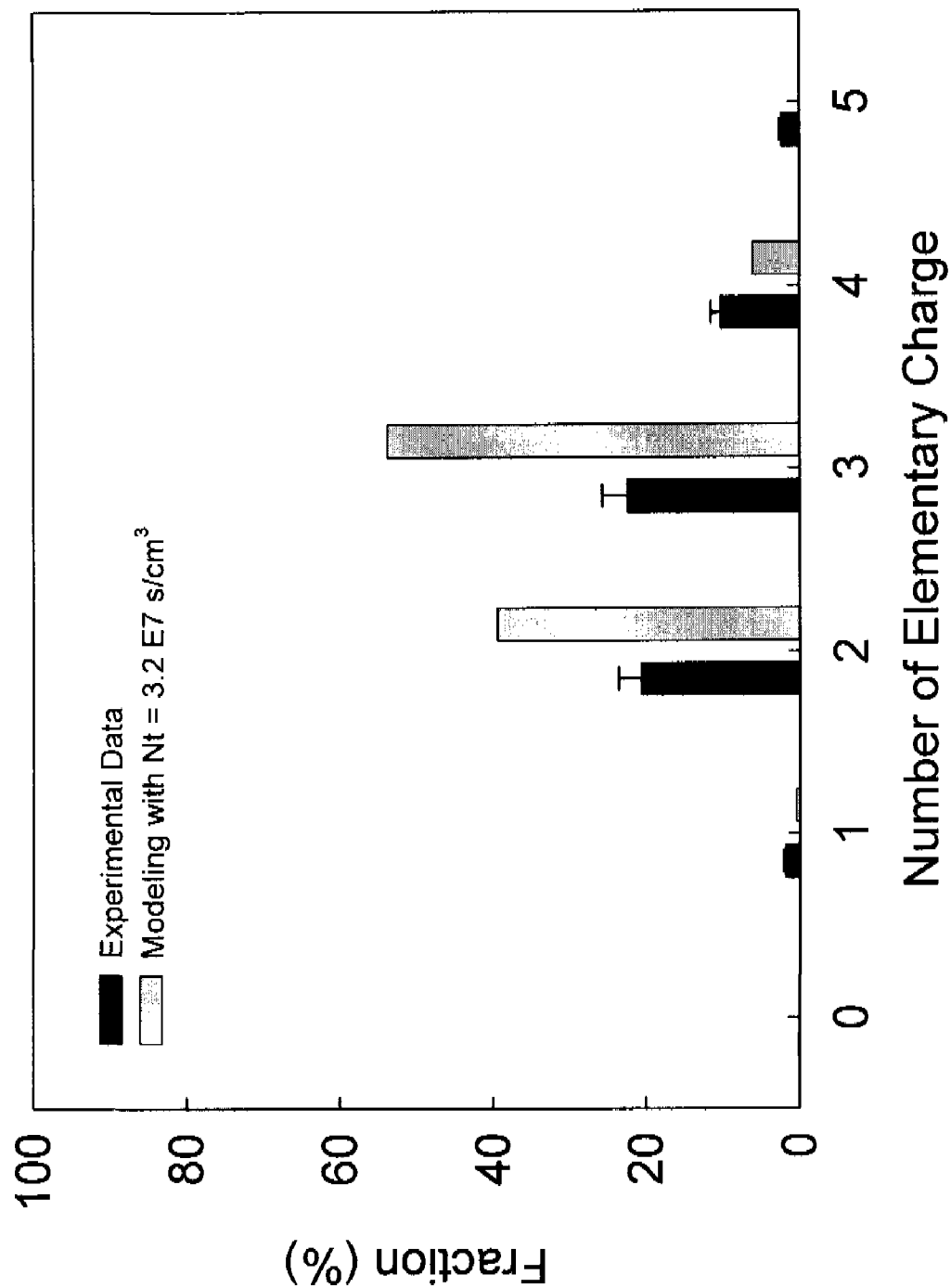
FIG. 14 is a graph illustrating the charge distributions of monodisperse test particles after passing through the unipolar mini-charger shown in FIGS. 3-6, with 50 nm diameter particles and a 0.3 lpm flowrate.
Figure 15:
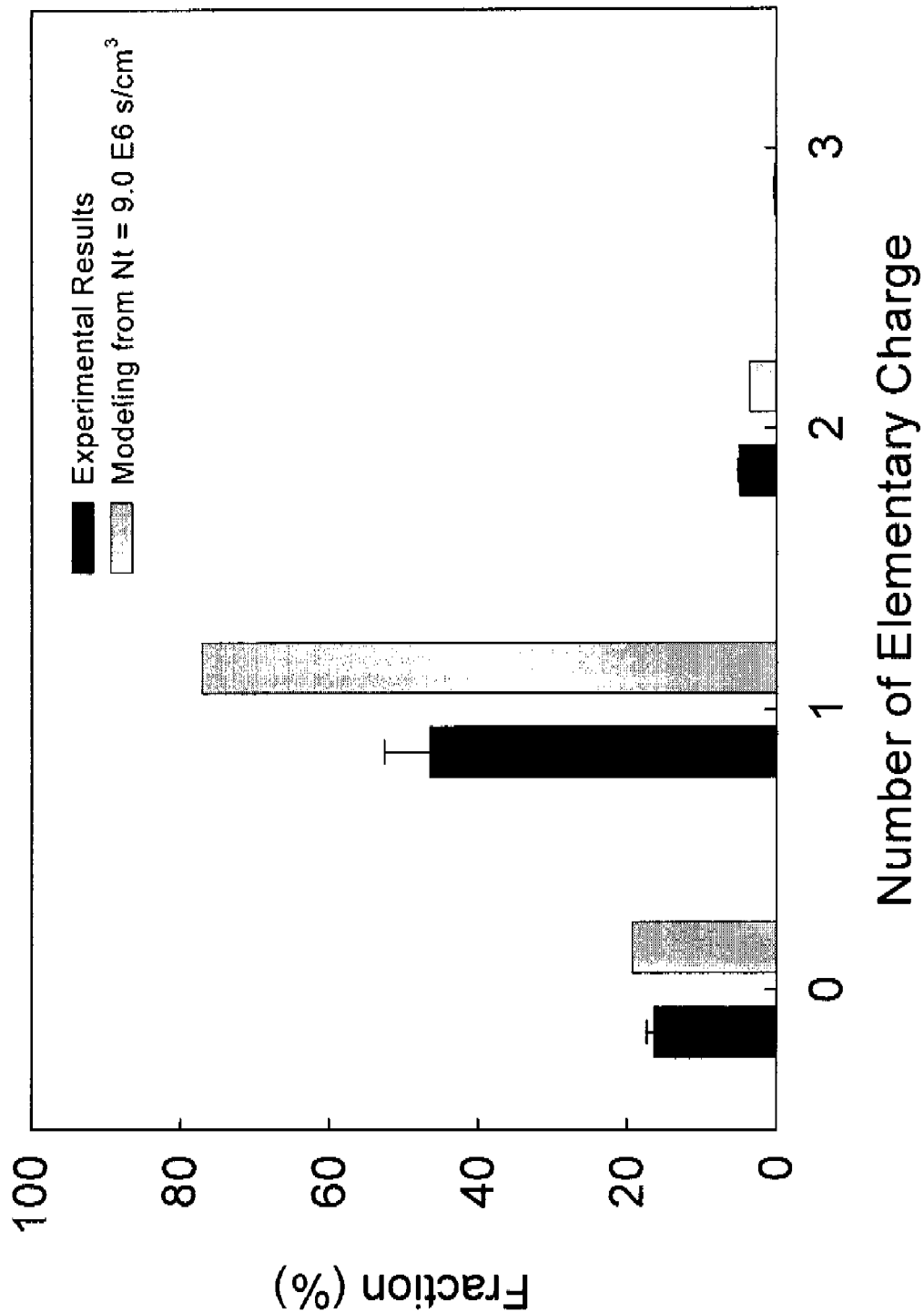
FIG. 15 is a graph illustrating the charge distributions of monodisperse test particles after passing through the unipolar mini-charger shown in FIGS. 3-6, with 20 nm diameter particles and a 1.5 lpm flowrate.
Figure 16:
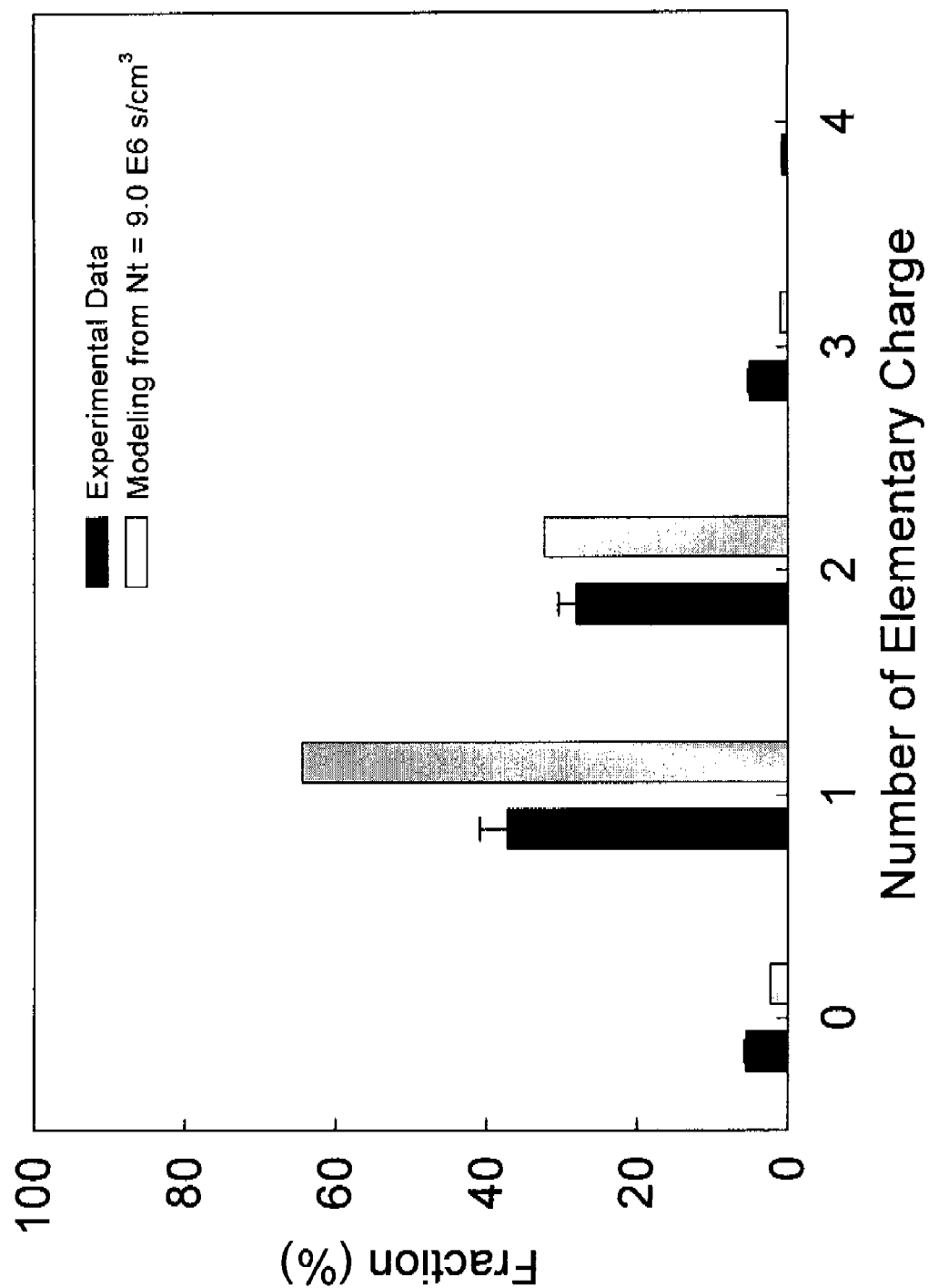
FIG. 16 is a graph illustrating the charge distributions of monodisperse test particles after passing through the unipolar mini-charger shown in FIGS. 3-6, with 35 nm diameter particles and a 1.5 lpm flowrate.
Figure 17:
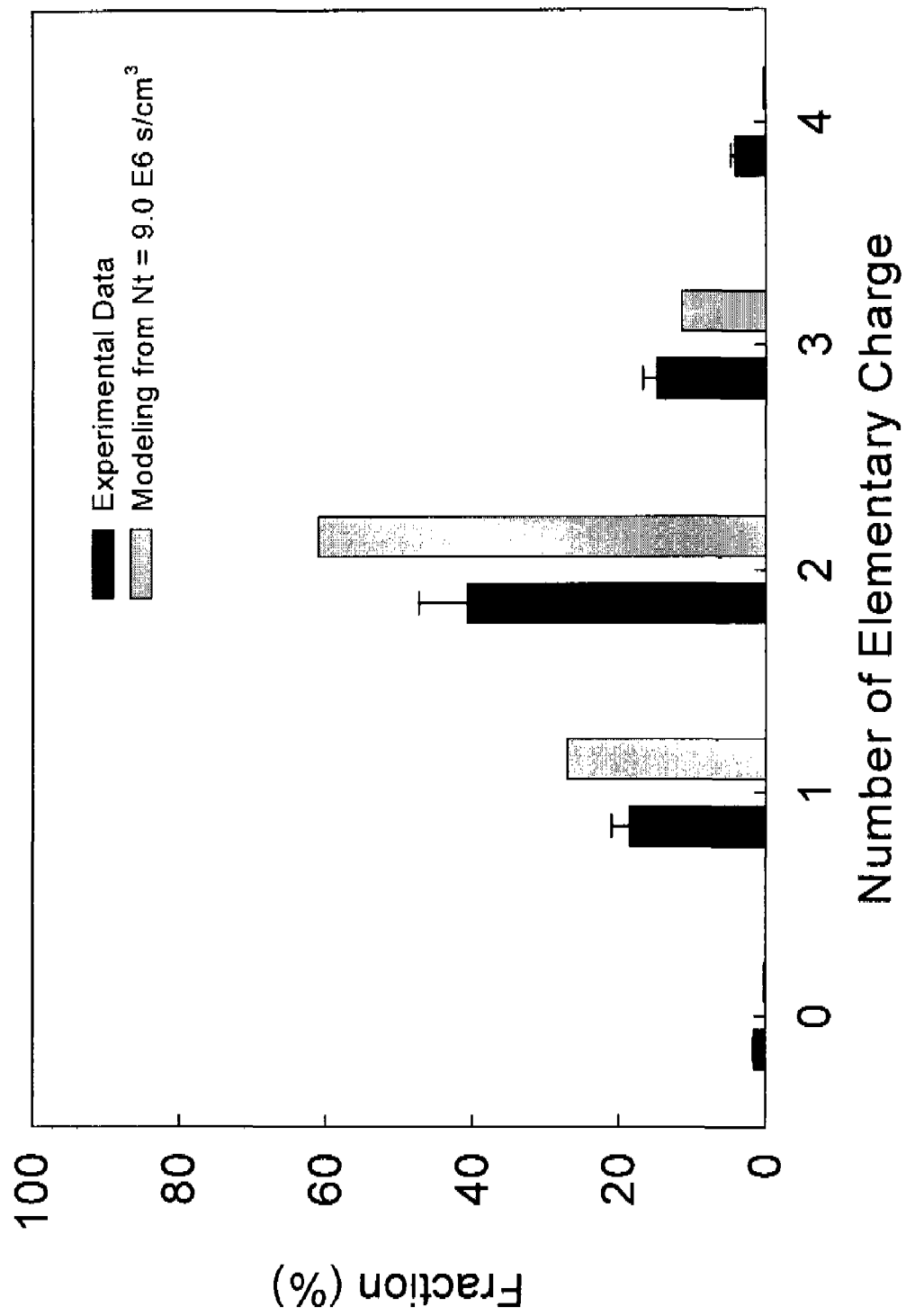
FIG. 17 is a graph illustrating the charge distributions of monodisperse test particles after passing through the unipolar mini-charger shown in FIGS. 3-6, with 50 nm diameter particles and a 1.5 lpm flowrate.

The example demonstrates that, for particles smaller than 15 nm, all the particles are singly charged. Multiply charged particles are observed at sizes larger than 15 nm. FIG. 12 shows the charge distributions of test particles with diameters of 20, 35 and 50 nm, for the aerosol flowrates of 0.3 and 1.5 lpm, respectively. Note that the experimental data plotted in FIG. 12 is extrinsic. As expected, particles of a given size acquire more electrical charges at the flowrate of 0.3 lpm than at the flowrate of 1.5 lpm, because of the higher particle residence time. Thus, for the particle size distribution characterization, it is desirable to operate the mini-charger at the flowrate of 1.5 lpm. On the other hand, it is more desirable to operate a miniaturized sensor at the flowrate of 0.3 lpm because of the reduced demand for air movement.

Also included in the FIGS. 12-17 are the calculated results using the particle charging model for the prediction of the intrinsic charging efficiency of the mini-charger at the 0.3 and 1.5 lpm flowrates. The $N_i t$ values for the two flowrates obtained in the prediction of intrinsic charging efficiency were used in this calculation. The model assumes spatially uniform and constant ion concentration in the mini-charger charging zone. No particle losses are considered in the model. The difference between the calculated and experimental data is attributed to the loss of particles and the invalid ion concentration assumption.

As described above, a corona-discharge based, unipolar aerosol mini-charger has been developed and demonstrated. The mini-charger is 1.0 inch length and 0.5 inch in diameter. The construction of the mini-charger includes at least two components. The outer tube, or case, includes a radial inlet tube and axial outlet tube. The second part is the corona discharge module, including a pointed tungsten needle electrode placed coaxially in an outer tube capped with a perforated dome. The corona module is installed in the case at the end opposite the axial exit tube, and is electrically insulated. Corona discharge is initiated in the module with a high voltage difference between the module case and the corona needle. The ion-transport voltage is established between the corona module and the outer case to direct unipolar ions into the particle charging zone. The compact size and simple construction makes the mini-charger suitable to integrate with other miniaturized aerosol devices based on the electrical mobility technique.

The compact size does not compromise the performance of the mini-charger, which demonstrates very good aerosol charging efficiency (both intrinsic and extrinsic) for particles ranging from the submicron to 10 nm. Experiments were performed to identify the operational settings to maximize the performance of the mini-charger (i.e., extrinsic charging efficiency) at two aerosol flowrates, i.e., 0.3 and 1.5 lpm. The optimized settings of the mini-charger are a corona current of 1 µA and an ion-transport voltage of 40 V for the 0.3 lpm flowrate; and 2 µA and 120V for the 1.5 lpm flowrate. These settings were then used in subsequent experiments to evaluate the charging performance of the mini-charger. The intrinsic charging efficiency for the 0.3 lpm flowrate is, in general, higher than that of the 1.5 lpm flowrate, due to the longer residence time of particles in the charging zone of the mini-charger. A 100% intrinsic charging efficiency of the mini-charger was achieved at particle sizes larger than 20 nm for the 0.3 lpm flowrate, and at 40 nm or larger for the 1.5 lpm flowrate. In both cases the intrinsic charging efficiency decreases with particle size. With regard to extrinsic charging efficiency, the observation of higher efficiency for 0.3 lpm than that for 1.5 lpm is reversed, because of lower particle losses in the charging zone at the high flowrate. The particle losses are attributable to the electrostatic and space charge effects. The reduced charged particle loss for the 1.5 lpm flowrate case more than compensates for the lower intrinsic charging efficiency. The net effect results in a higher extrinsic charging efficiency. The extrinsic charging performance of the mini-charger when operated at the 1.5 lpm flowrate matches that of the unipolar aerosol charger in which an AC electrical field and sheath flow were implemented to reduce particle losses.

For the two flowrates evaluated, multiple charges on individual particles were observed for particles larger than 15 nm. Charge distributions of monodisperse test particles were measured. Information about charge distributions of particles after passing through the mini-charger is used to retrieve the particle size distributions from the measured penetration data with the data-reduction scheme in the miniaturized nanoparticle sizer.

Figure 18:
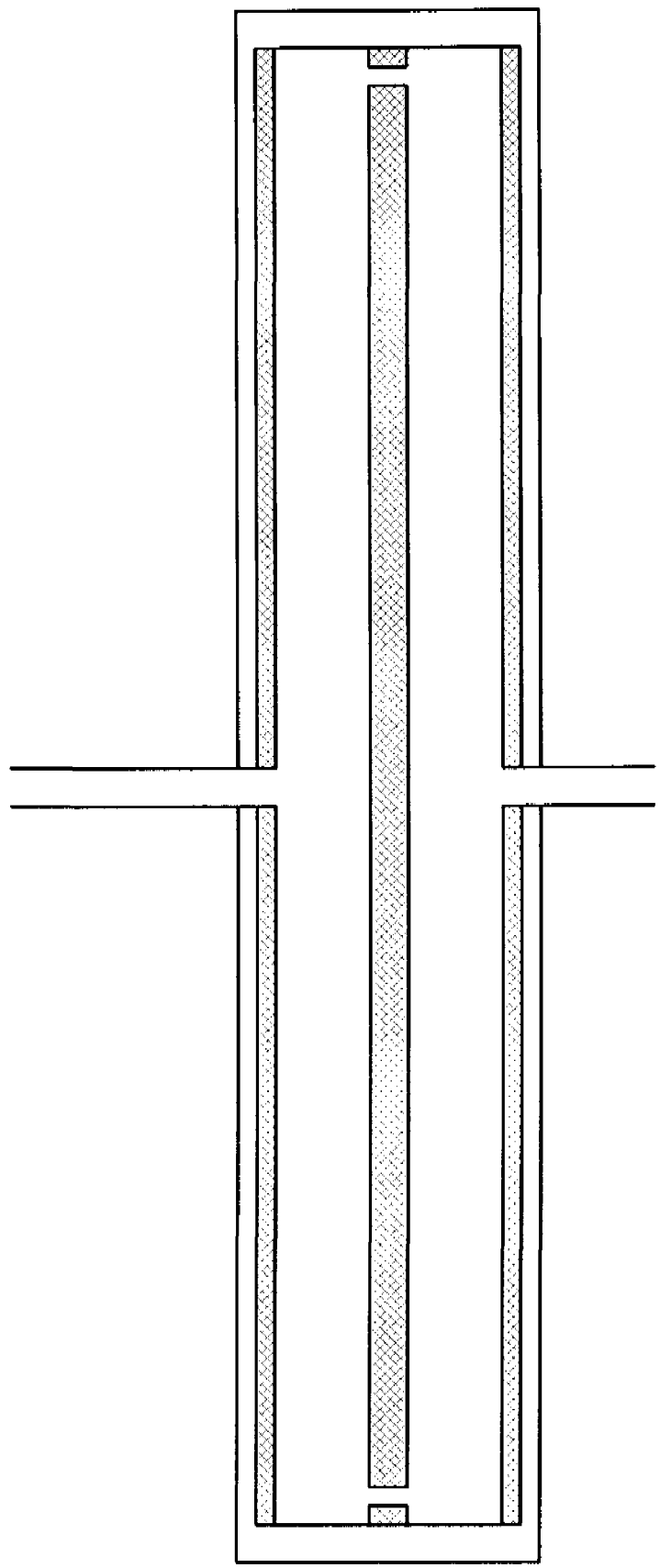
FIG. 18 is a schematic diagram of a mini-disk nanoparticle classifier that may be used with the mini-nanoparticle sizers shown in FIGS. 1 and 2.
Figure 19:
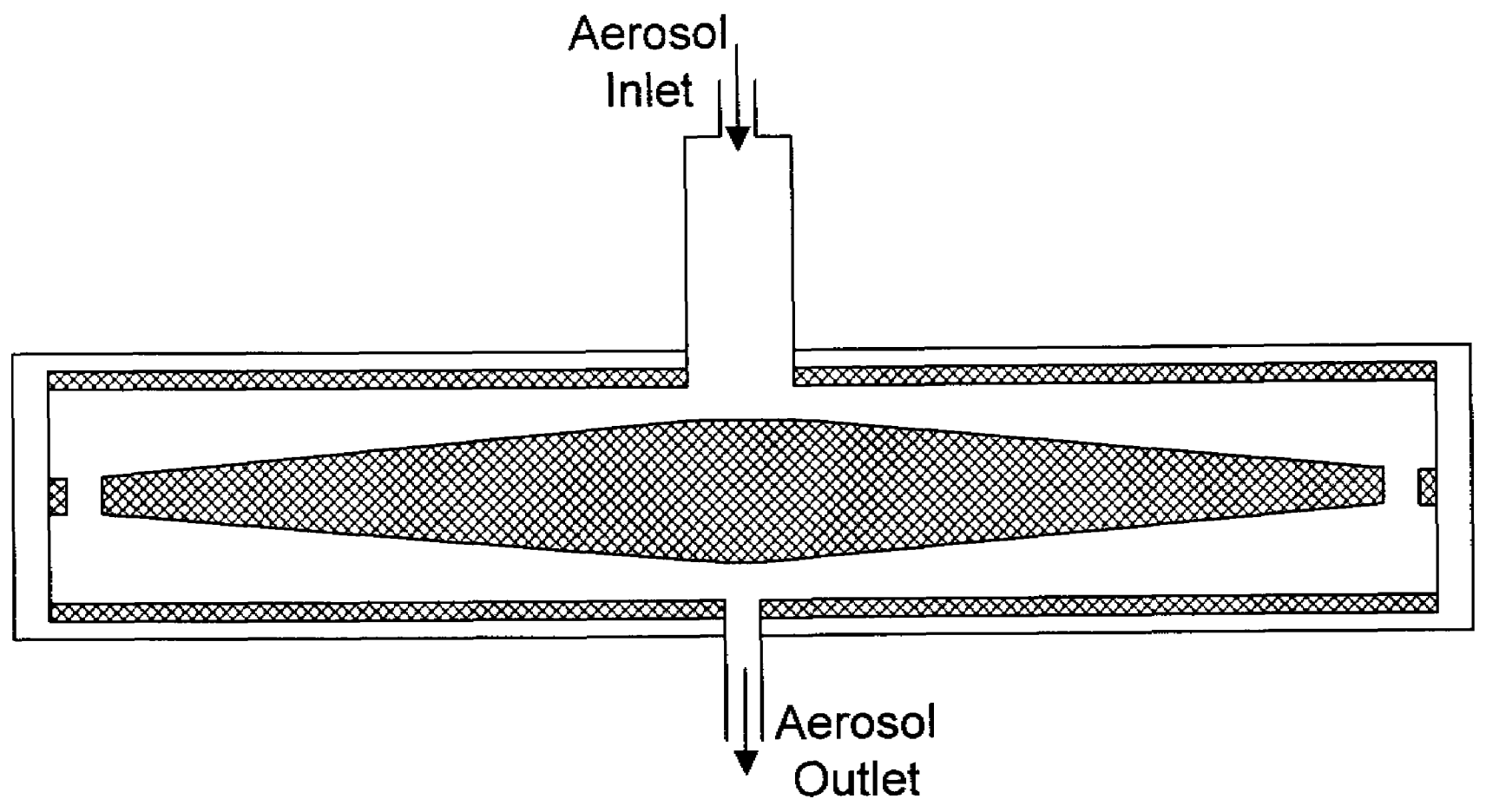
Figure 20:
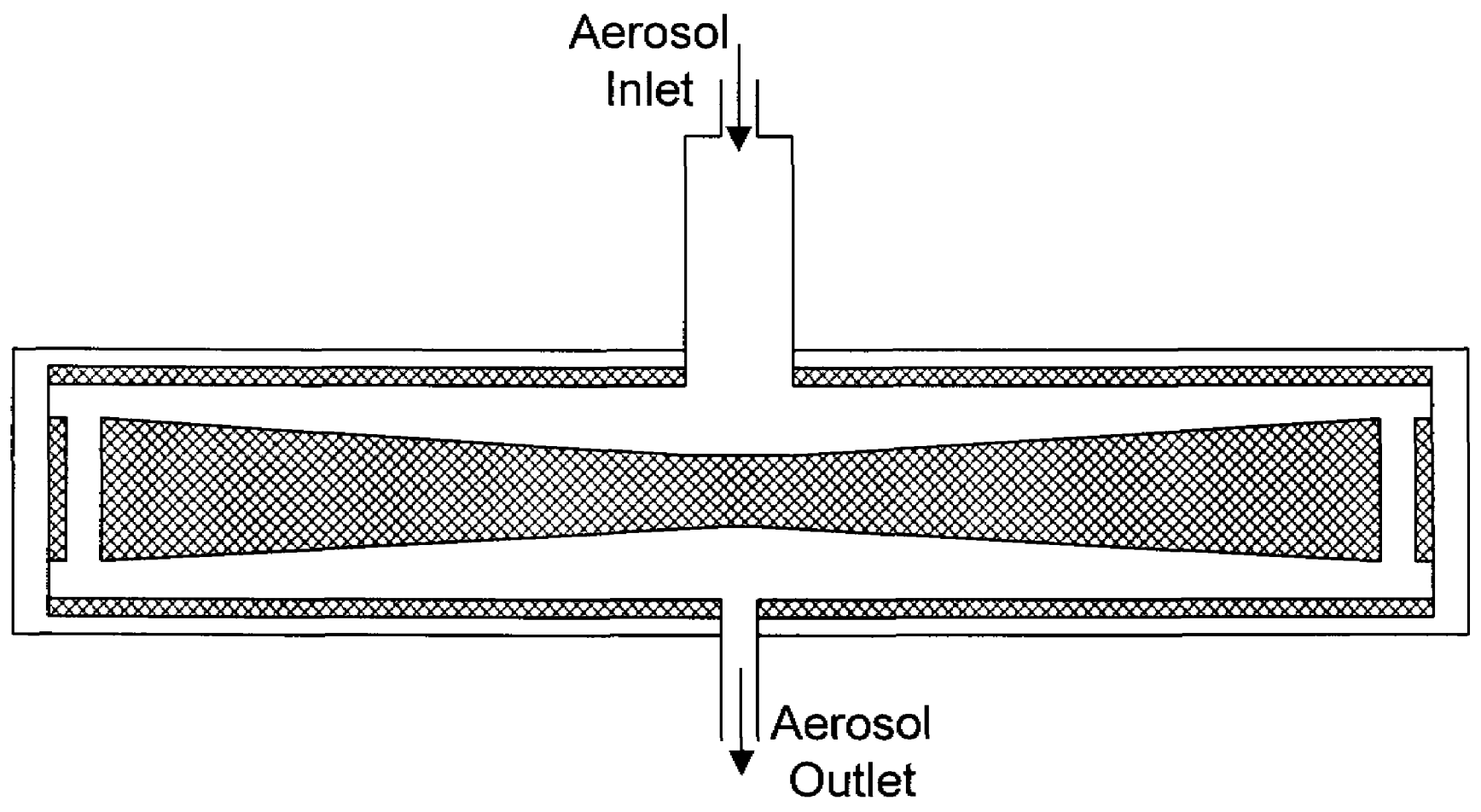
Figure 21:
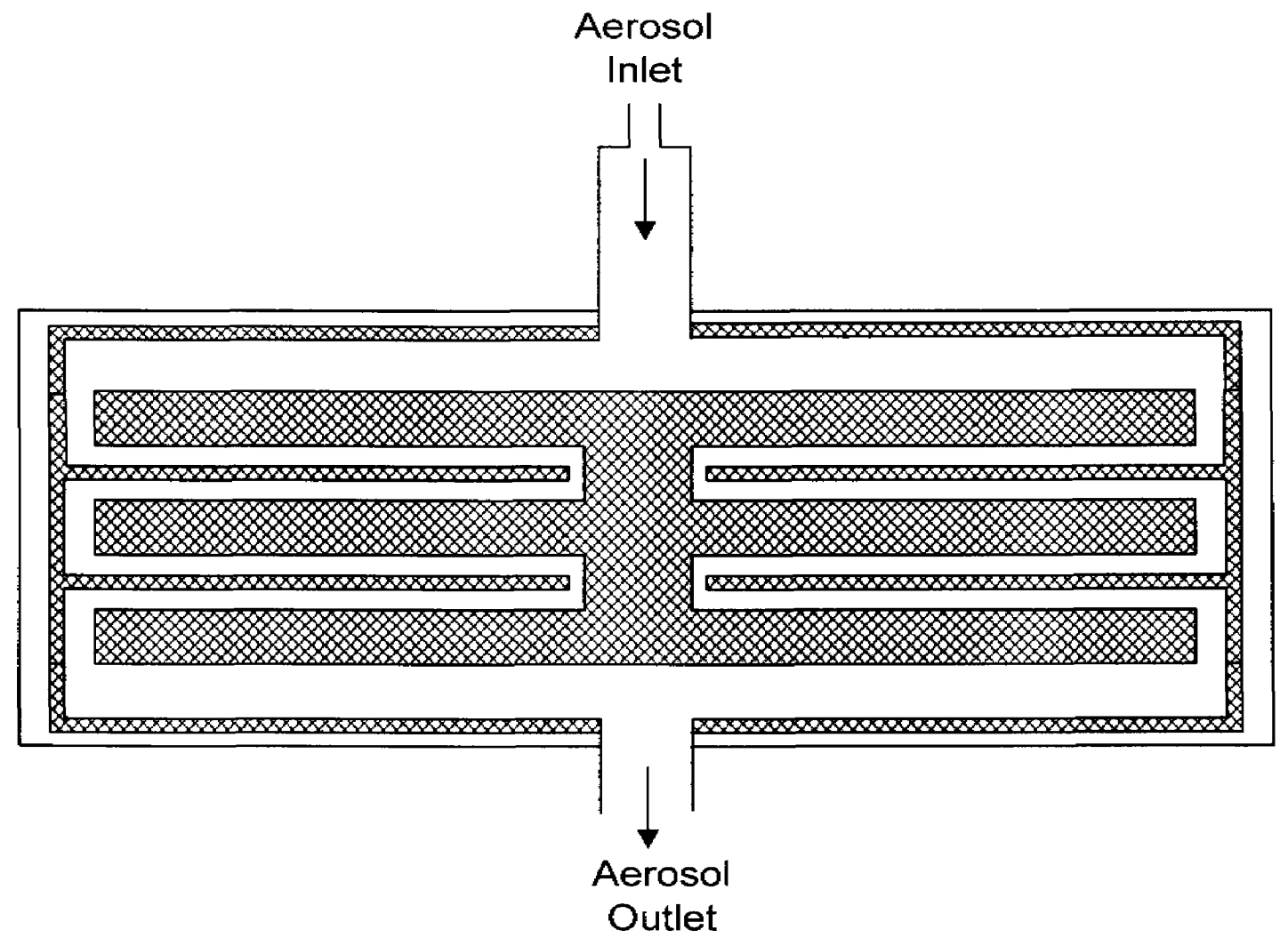

An exemplary embodiment of the mini-disk nanoparticle classifier is shown in FIG. 18. Alternative embodiments of the classifier are shown in FIGS. 19-23. The alternative embodiments illustrate that the classifier may include more than one disk and/or may include disks shaped to channel charged particles towards the electrometer (shown in FIGS. 1 and 2). The mini-disk nanoparticle classifier (MDNC) includes a technology for characterizing and sorting aerosol particles in the submicron size range. The underlying physical basis is that of electrical mobility classification. A particle's electrical mobility expresses the ratio of viscous to electrostatic forces that it experiences, and is a function of both its size and electrical charge state. If either quantity is known, the other may be determined by this device. The MDNC differentiates mobilities by virtue of the unique relationship between mobility and particle spatial trajectory that results within the device. In the exemplary embodiment, the MDNC provides two independent control chambers that allow the mobility sorting characteristics of the device to be optimized. The interplay of various features of the MDNC are well suited to providing an overall device of small spatial scale (i.e., miniaturized relative to existing technologies) that operates at modest applied voltages, while retaining favorable resolution for mobility discrimination and minimizing internal losses.

The MDNC is utilized to characterize the size of submicron particles by sorting their electrical mobilities. Sorting is accomplished by exploiting the differing spatial trajectories that result when particles of differing electrical mobilities are subject to an imposed electric field. The MDNC includes an outer body forming two cavities or control chambers. The two control chambers are separated by a plate, barrier, or membrane. The dimensions of the two cavities need not be symmetric. The aerosol sample enters and exits through tubes located at the extrema of the two chambers. Permeations in the separating plate or barrier form a series of fluidic passages that allow the sampled flow to pass from the first control chamber into the second control chamber. The range of particle mobilities that will pass through the permeations, and thus pass from the first to the second control chamber, is determined by the relationship between the geometry of the permeations, the dynamics of the fluid flow within the control chambers, and/or the potential voltage established across each of the two control chambers. The range of particle mobilities that will exit the MDNC is also determined by the relationship between the geometry of the exit tube, the dynamics of the fluid flow within the second control chamber, and/or the electric field distribution within the second control chamber. These dependencies allow the mobility sorting characteristics of the two control chambers to be controlled independently. This feature allows optimization of the steepness of the mobility passband as a function of particle mobility.

The particles of interest are entrained in an aerosol flow. A sample of this flow enters the MDNC via an upper inlet tube into the first control chamber. The flow then passes through permeations in the separating barrier before entering the second control chamber. The design of the permeations results in a specified value of flow Reynolds number to control the fluid dynamics both with in volume of the permeation, and the flow exiting the permeations and entering the second control chamber. The flow exits the MDNC via a lower outlet tube in the second control chamber. An embodiment of the separating barrier is a disk containing a radial annulus of cylindrical through-holes. The number, diameter, and length of the holes, and/or the volumetric flow through the MDNC determine the flow Reynolds number within the volume of the holes and that entering the second control chamber. The diameter of the holes, the radius of the annulus, the electric field imposed within the chambers, and the flow velocities within the control chambers controls the range of mobilities that will pass through the cylindrical through-holes.

An axial electric field is independently established in either or both control chambers. The electric field is established by imposing a potential difference between the separating plate or barrier, and plates or surfaces located at the opposite ends of each respective control chamber. The planar geometry of the separating plate or barrier and the chamber end plates or surfaces results in a uniform, axial electrical field in both control chambers of the MDNC.

The classifier embodiment shown in FIG. 23 includes a top metal plate and a middle metal disk melted with a bottom metal plate, separated by an electrically insulating spacer to create a flow chamber with a height of approximately 1/16 inch. An annulus of three slots is located close to the outer edge of the middle disk. An electrically charged aerosol stream is introduced into the top flow chamber through the central tube connected to the middle plate. The sheath flow is introduced into the top flow chamber through the side tube connected to the top plate. The other central tube connected to the bottom plate is used as the flow exit. Voltage may then be applied through a high voltage cable connected to the bottom plate which is melted with the middle plate. The top metal plate is electrically grounded. The applied voltage establishes an electrical field in the top flow chamber. The aerosol enters the device from the top central tube, mixed with the sheath air from the side tube into the top flow chamber, moves outwards radially, passes through the slots, and converges radially to the opposite central exit tube. When a fixed electrical field is established on the top flow chamber, the trajectories of charged particles are deflected. All particles with sufficiently large electrical mobilities will be deposited on the top plate, and those with sufficiently small mobilities will fully escape and exit the device. Particles with the middle mobilities will partially deposited on the top plate.

In an embodiment, the mini-disk electrostatic aerosol classifier weighs approximately 24 grams, and its design and dimensions are shown in FIG. 22. The basic construction sandwiches the middle metal disk between symmetric top and bottom metal plates, using electrically insulating spacers to create two equal flow chambers 0.05 inch high (1.27 mm). An annulus of small orifices is located close to the outer edge of the middle disk, connecting the top and bottom flow chambers. An electrically charged aerosol stream is introduced into the top flow chamber through the central tube connected to the top plate. The other central tube connected to the bottom plate is used as the aerosol flow exit. Voltage may be applied through a high voltage cable connected to the outer edge of the middle disk. The top and bottom metal plates may be either electrically grounded or biased to separate potentials with respect to the middle disk. This option allows users to configure the device to establish independent electrical fields in either flow chambers. The aerosol enters the device from one of the central tubes, moves outwards radially, passes through the orifices, and converges radially to the opposite central exit tube.

When a fixed voltage is applied on either chamber, the trajectories of charged particles are deflected by the resulting electric field. All particles with sufficiently large electrical mobilities will be deposited on the plates, and those with lower mobilities will partially or fully escape and exit the device. When integrated into the nanoparticle sizer, a sensitive aerosol electrometer may be used downstream of the device to measure the concentration of escaped charged particles. In this study, we focused on the laboratory evaluation of the classifier's performance, so an Ultrafine Condensation Particle Counter (UCPC), such as a model 3025A UCPC commercially available from TSI Incorporated, was used to detect particle number concentration.

FIG. 24 is the schematic diagram of the experimental setup for the evaluation of an example disk electrostatic aerosol classifier. The disk classifier was tested with laboratory generated test particles in the size range of 10-200 nm, both neutral and charged. Monodisperse test particles (NaCl) in the size range of 50-200 nm were produced using an atomizer-Differential Mobility Analyzer (DMA)-classification technique. For particles of diameters less than 50 nm, monodisperse silver particles were generated by an evaporation-condensation-DMA-classification technique with a tube furnace. For all particle sizes, the transmission efficiencies through the disk classifier with the disk and all plates electrically grounded were measured for both singly charged and neutral particles. Electrically neutral particles were obtained by passing charged particles classified by a DMA, through a $Po^{210}$ neutralizer and a home-made charged particle remover, including a high voltage electrode and a grounded outer housing. Particle number concentrations upstream and downstream of the disk classifier, $N_{up}$ and $N_{dn}(0)$, were measured by a UCPC operated at the low flow mode (0.3 lpm), and the particle transmission efficiency was then obtained as the ratio of $N_{up}$ and $N_{dn}(0)$ shown as:

$$\text{Transmission} = \frac{N_{up}}{N_{dn}(0)} \quad (3)$$

When measuring the cut-off curves, monodisperse singly-charged particles were directly fed into the device. For each test particle size, the particle concentration downstream of the disk classifier with no voltage applied, $N_{dn}(0)$, was first measured. Corresponding downstream particle concentrations, $N_{dn}(V)$, were then measured at a sequence of applied voltages. As the applied voltage is increased, more charged particles were precipitated. For each new voltage setting, $N_{dn}(0)$ was measured again to account for possible drift in the stability of test particle concentration. The particle cut-off curve for a given particle size is given by the particle penetration, defined in the following equation, as a function of the applied voltage.

$$P = \frac{N_{dn}(V)}{N_{dn}(0)} \quad (4)$$

In the measurements of both particle transmission and cut-off curves, the flowrate through the disk classifier was set at 0.3 lpm and controlled by the UCPC operated in the low flow mode. A lower flow rate enables use of a lower voltage to precipitate all the particles with a given electrical mobility, and consequently reduces the size of the air mover. This further translates into energy saving and improvement of device portability for the targeted applications.

Figure 22:
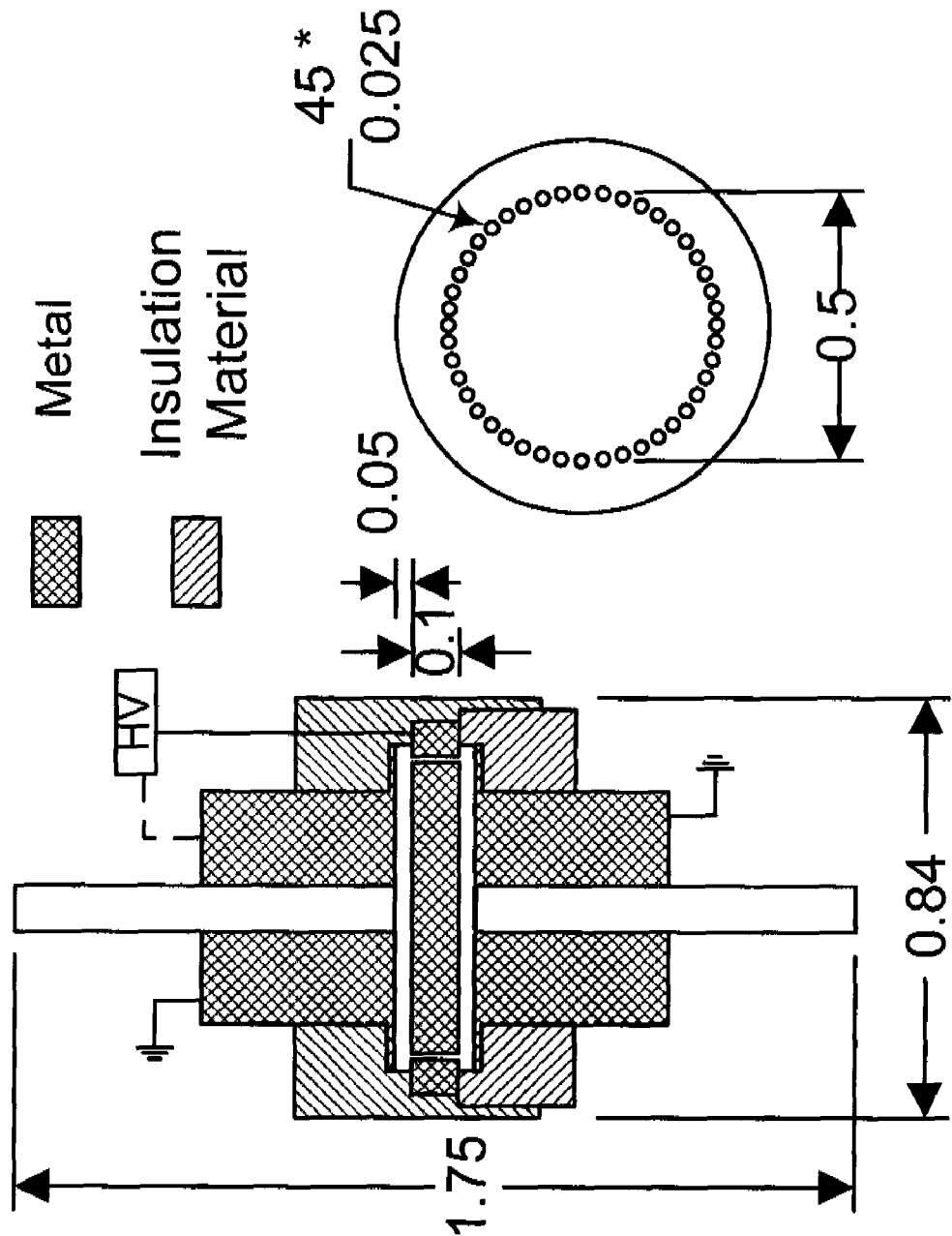
FIG. 22 is a schematic diagram of a fourth alternative embodiment of a mini-disk classifier that may be used with the mini-nanoparticle sizers shown in FIGS. 1 and 2.
Figure 23:
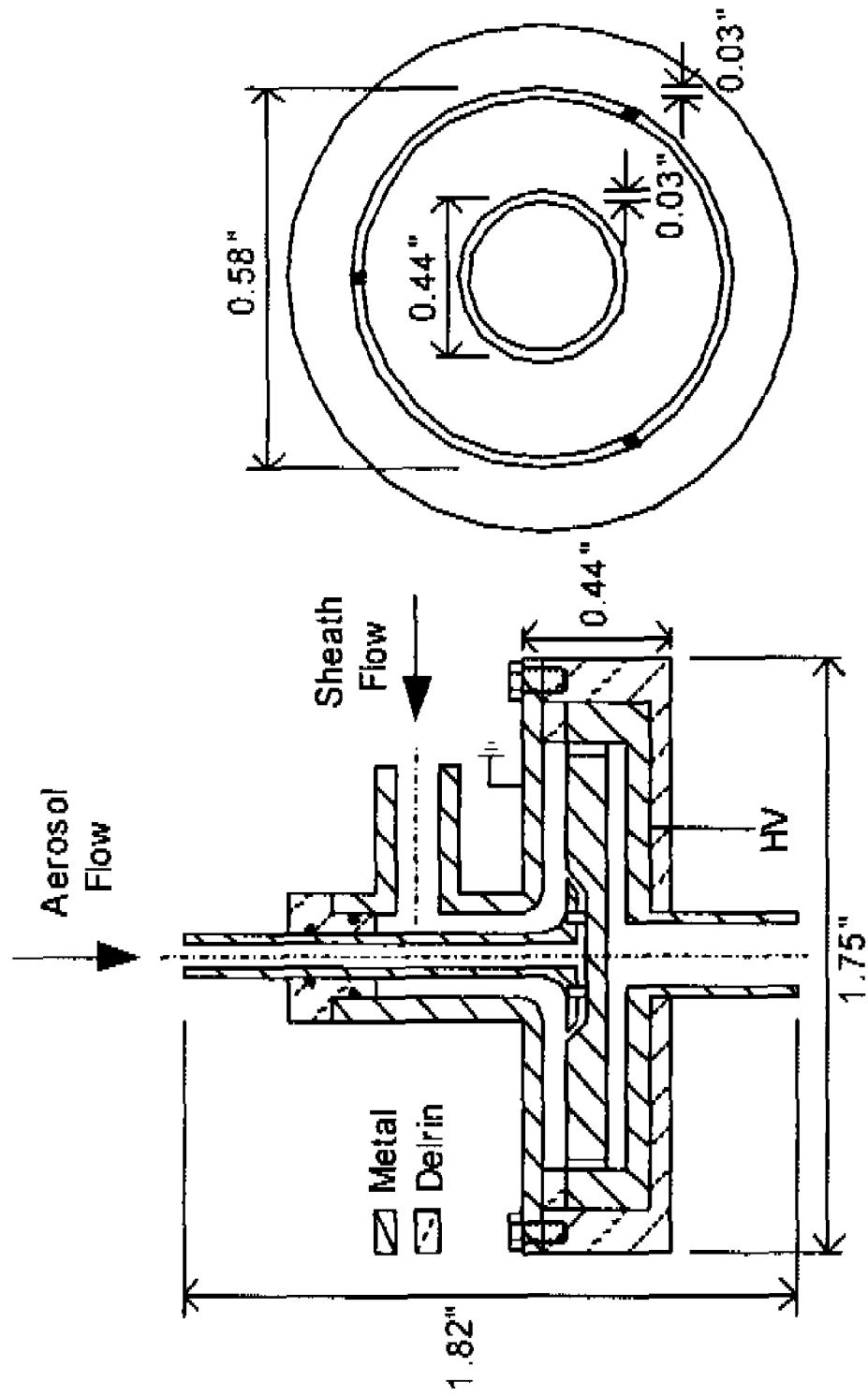
FIG. 23 is a schematic diagram of a fifth alternative embodiment of a mini-disk classifier that may be used with the mini-nanoparticle sizers shown in FIGS. 1 and 2.
Figure 24:
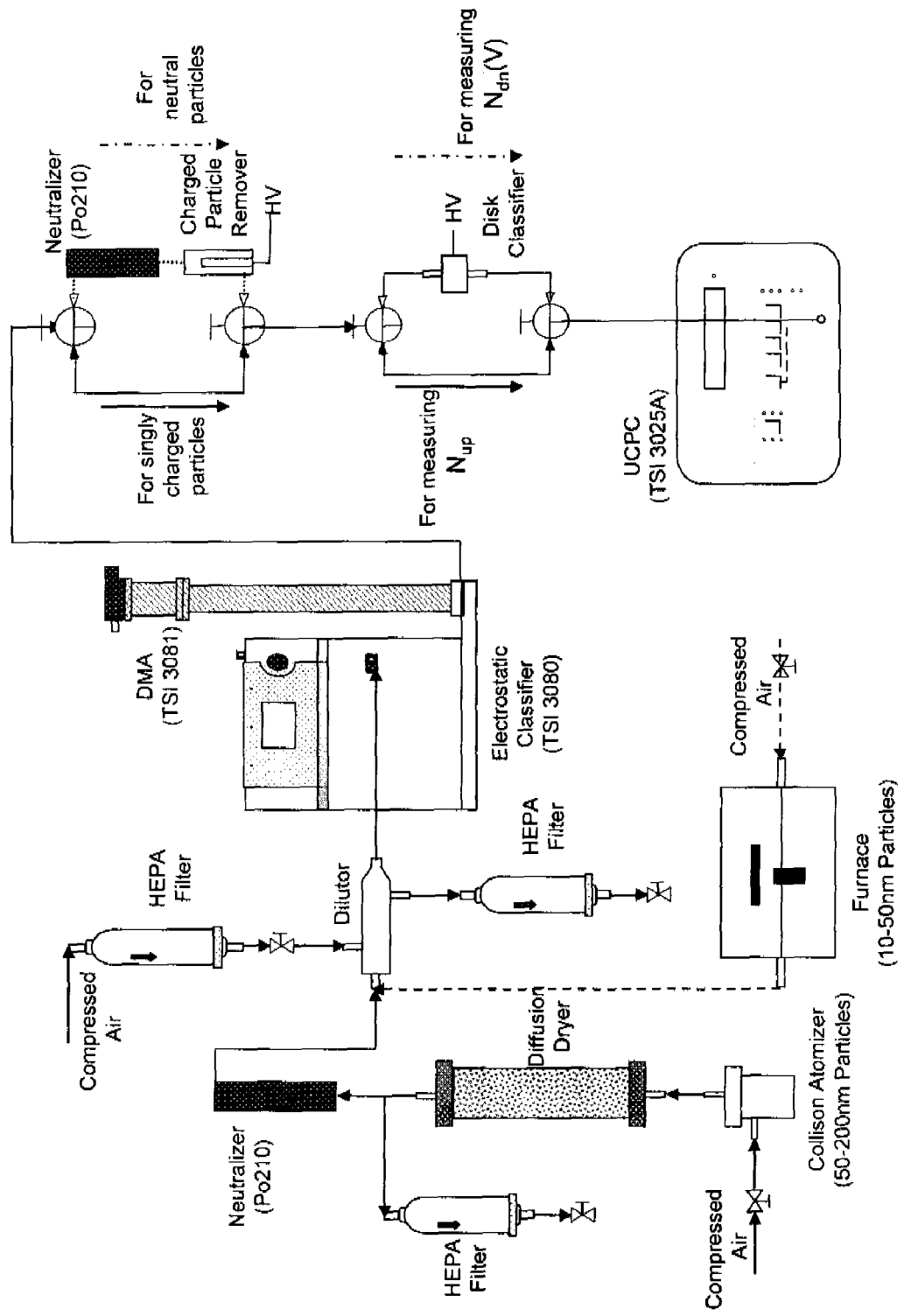
FIG. 24 is a schematic diagram of an experimental setup for a performance evaluation of the mini-disk classifiers shown in FIGS. 18-23.

Particle penetration measurements have been performed for two reasons. One concern in developing a compact aerosol classifier is particle loss. As shown in FIG. 22, the size of the flow chambers between the end plates and middle disk are much reduced. Even without the voltage applied, charged particles could be deposited by electrical image forces if they travel close to the grounded metal plates. The second reason for performing particle penetration measurements is that the data will be used in the data reduction process to recover the particle size distributions being sampled.

Figure 25:
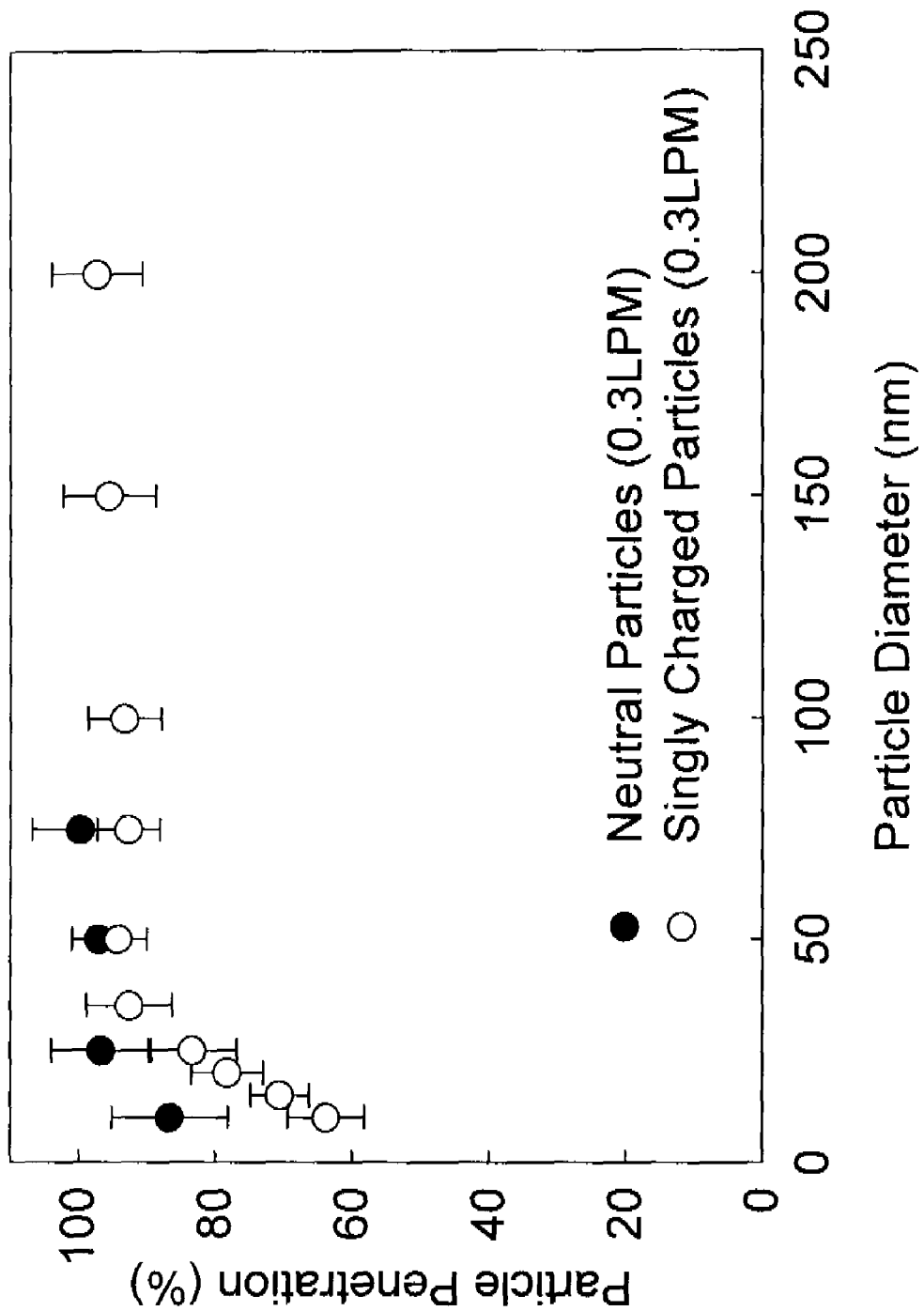
FIG. 25 is a graph illustrating the penetration of neutral and singly-charged particles in the mini-disk aerosol classifiers shown in FIGS. 18-22.
Figure 26:
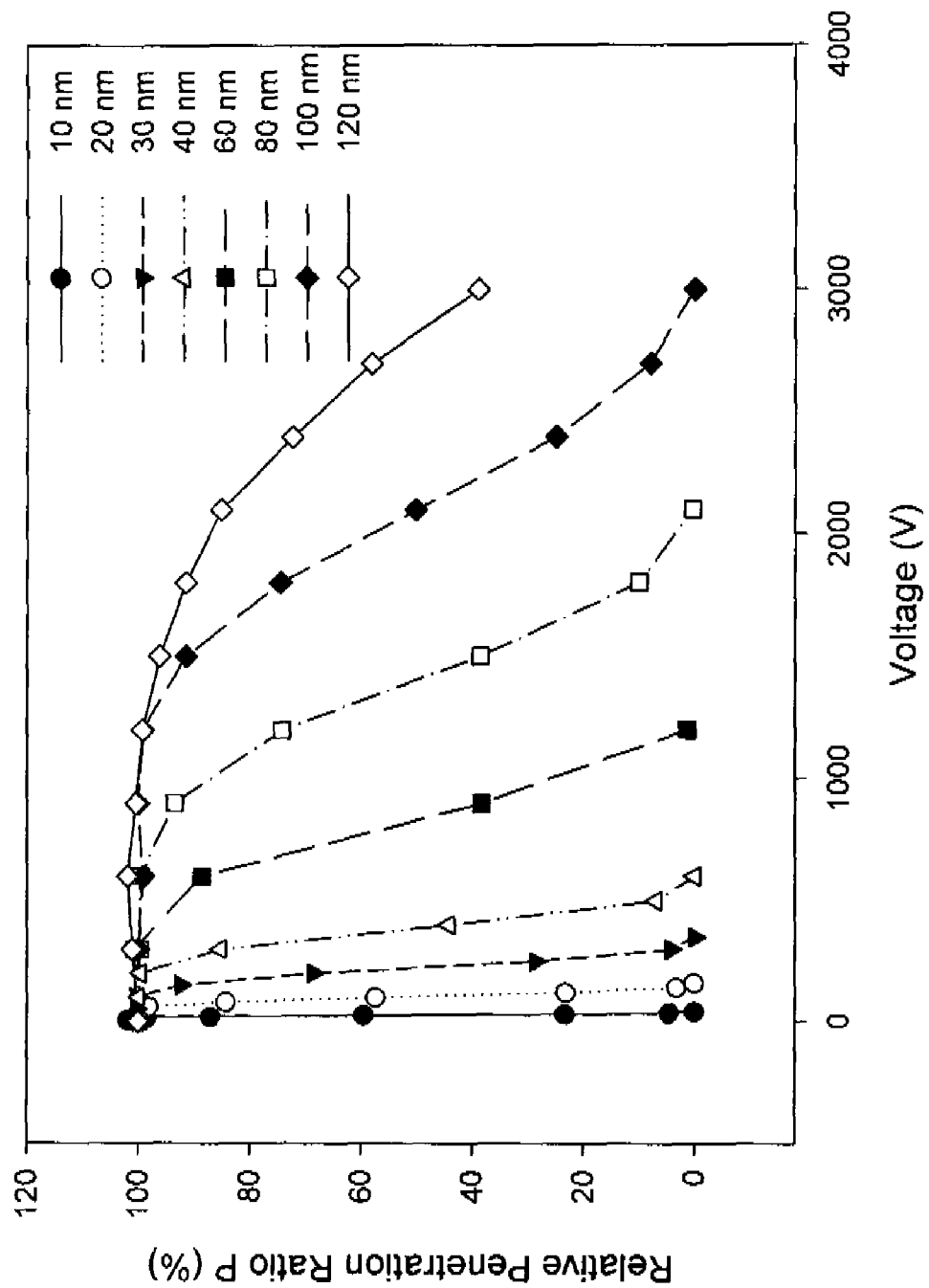
FIG. 26 is a graph illustrating the penetration of neutral and singly-charged particles in the mini-disk aerosol classifier shown in FIG. 23.

The experimental particle penetration through the disk aerosol classifier for singly charged and neutral particles is shown in FIG. 25. Monodisperse particles between 10 to 200 nm were used for these measurements. More than 85% penetration is measured for neutral particles larger than 10 nm. The loss of neutral particles is solely due to diffusion. A greater proportion of charged particles are lost than neutral particles. This tendency is especially marked for particles smaller than 50 nm. The loss of singly charged particles increases as particle size reduces. It indicates, in addition to the particle diffusion, that image forces do play the role in the loss of charged particles. At 10 nm in diameter the particle penetration through the classifier reduces to 64%, which is still considered enough for subsequent precipitation measurement and analysis. Similarly, FIG. 26 shows the particle cut-off curves for different particle sizes at 0.5 lpm aerosol flowrate and 1.5 lpm total flowrate using the embodiment shown in FIG. 23. As shown in FIG. 26, the penetration is normalized to 100% with no voltage applied. As expected, larger particles require higher voltage than smaller particles to achieve the same penetration. The results demonstrate that this device is capable of differentiating particles of different sizes by virtue of their electrical mobilities. When integrated into the nanoparticle sizer, a sensitive aerosol electrometer can be used downstream of the device to measure the concentration of escaped charged particles.

Figure 27:
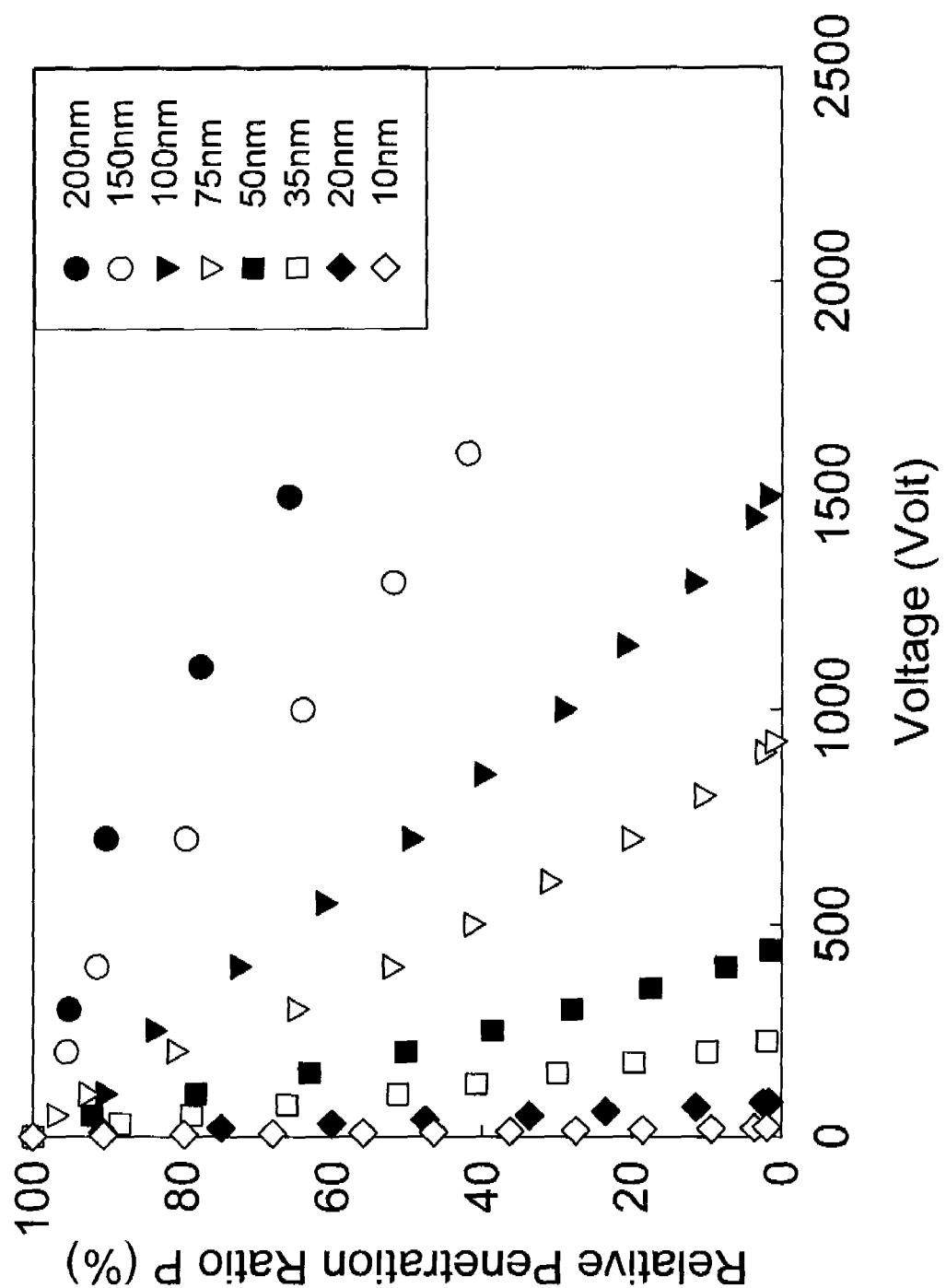
FIG. 27 is a graph illustrating the particle cutoff curves of the mini-disk classifier shown in FIGS. 18-22 for single chamber precipitation with a flowrate of 0.3 lpm.

Given the geometry of the classifier, at a fixed operational flowrate the performance is characterized by the particle cut-off curve or transfer function (e.g., the particle penetration as a function of voltage applied to the middle disk). Although the aerosol classifier is designed to make use of both flow chambers, it is useful to evaluate its performance when electrical field is established in only one flow chamber. This condition was used to investigate the basic device performance, and to evaluate the presence of possible manufacturing defects. For this evaluation, the top plate with the inlet tube was electrically grounded, and both the middle disk and the bottom plate with the outlet tube were set at the same voltage. FIG. 27 shows the particle cutoff curves for different particle sizes. The penetration is normalized to 100% with no voltage applied. As expected, larger particles use a higher voltage than smaller particles to achieve the same penetration. The results demonstrate that the disk classifier is capable of differentiating particles of different sizes by virtue of their electrical mobilities. Further, penetration is a linear function of the applied voltage for a given particle size. This result is consistent with the performance of much larger electrostatic classifiers.

Figure 28:
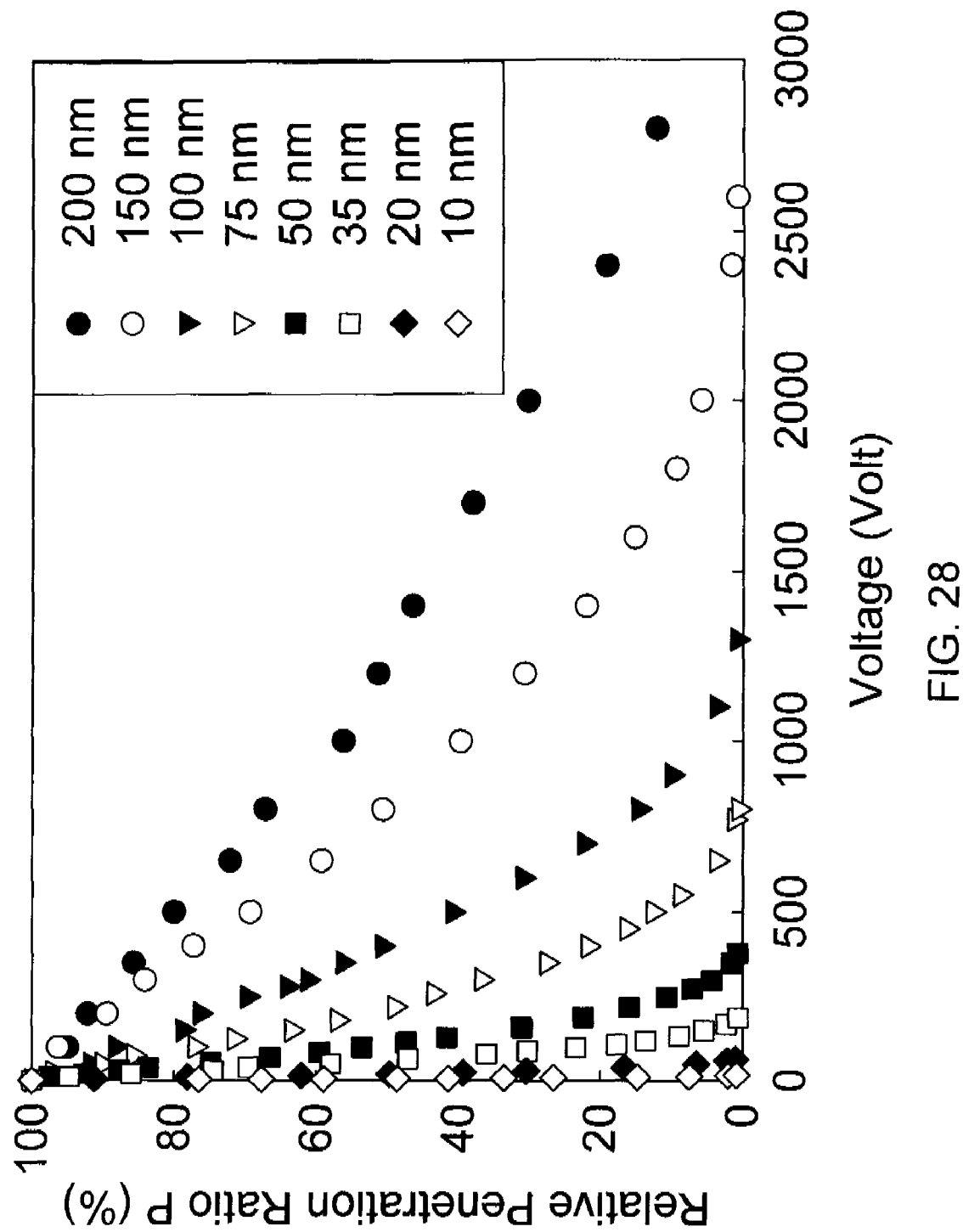
FIG. 28 is a graph illustrating the particle cutoff curves of the mini-disk classifier shown in FIGS. 18-22 for dual chamber precipitation with a flowrate of 0.3 lpm.

The miniaturization of the classifier is a primary advantage of the presently described invention. Making use of the flow chambers located at the top and bottom of the middle disk in the device is thus proposed for particle precipitation. This is obtained by applying a high voltage on the middle disk and keeping both top and bottom plates electrically grounded. The proposed operation also reduces the maximum voltage for completely depositing particles of a given electrical mobility. The experimental particle cutoff voltage curves using both flow chambers are shown in FIG. 28, and exhibit similar trends to those seen in FIG. 27. In contrast, however, the particle cutoff curves appear slightly nonlinear. The non-linearity is due to the mixing and redistribution of particle concentration after the aerosol stream passes through the small orifices to enter the bottom chamber of the classifier. Particles emerging from the top chamber have a non-uniform spatial distribution due to the deflection and precipitation of charged particles by the electric filed. Remixing of this non-uniform aerosol stream in the orifices presents the second chamber with a newly uniform stream. As described below, results for both single and dual chamber experiments were modeled.

There are at least two motivations for developing models to predict the particle cutoff curves. The first is to understand the fundamental precipitation mechanisms affecting this miniaturized aerosol classifier. The second is that the models, once experimentally verified, may be applied to estimate the upper particle size limit of the classifier when the operational condition changes, and to predict the particle cutoff curves of different particle sizes. The latter are used in the data-reduction process to obtain particle size distributions.

Figure 29:
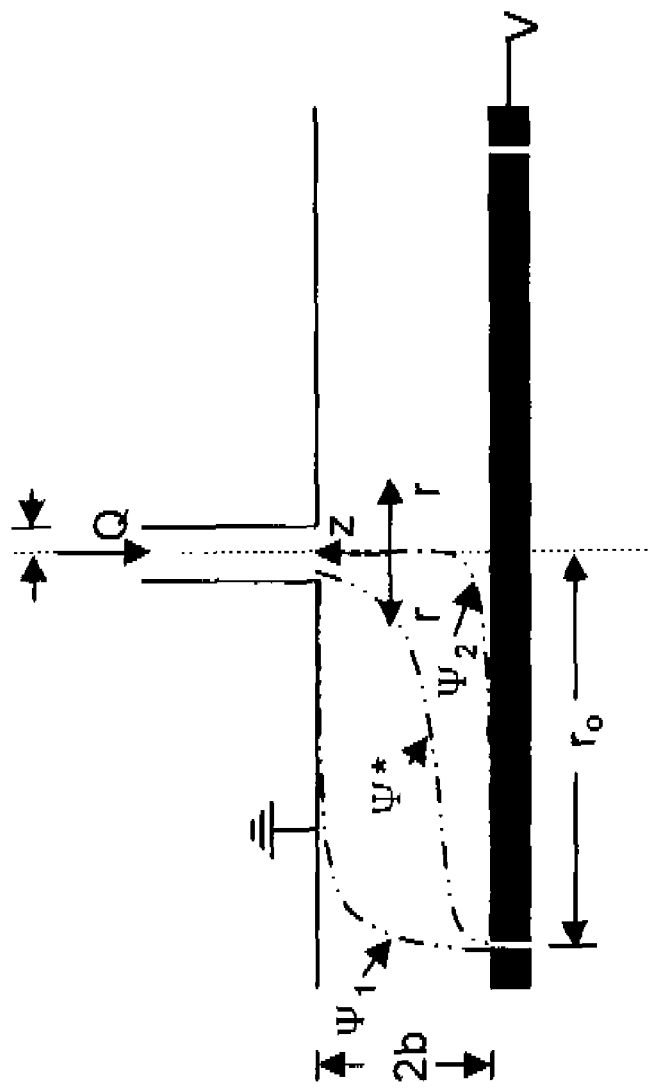
FIG. 29 is an illustration of the top flow chamber to be modeled in the mini-disk classifier shown in FIGS. 18-22, where charged particles are precipitated when an electrical field is established.

FIG. 29 shows the simplified aerosol classifier geometry used for model development. Only the top flow chamber of the device is considered in this example. Cylindrical coordinates are used, with r and z denoting the radial and axial coordinates, respectively. Neglecting particle inertial and Brownian motion, the particle trajectories are governed by the following equations:

$$\frac{dr}{dt} = u_r + Z_p E_r \tag{5}$$

$$\frac{dz}{dt} = u_z + Z_p E_z \tag{6}$$

where $Z_p$ is the electrical mobility of the particle, $u_r$ and $u_z$ are radical and axial components of the flow velocity, $E_r$ and $E_z$ are the respective components of the electrical field. In this case, it is assumed that the electrical field is uniform in the axial direction. $E_r$ is thus equal to zero everywhere, even at the edges of the orifices and inlet tube.

Non-diffusive particles are known to traverse their similar device along trajectories of constant particle stream function, $$\Gamma(r,z) = \psi(r,z) + Z_p \Phi(r,z) \tag{7}$$

which is expressed in terms of the fluid stream function, $\psi$, and the corresponding electric flux function, $\Phi$. With the assumption that the flow is axisymmetric, laminar, and incompressible, the stream function and electric flux function may be defined by the following equations:

$$\psi(r,z) = \int^{r,z}[ru_r dz - ru_z dr] \tag{8}$$

$$\Phi(r,z) = \int^{r,z}[rE_r dz - rE_z dr] = \int^{r,z}[-rE_z dr] \tag{9}$$

Because the particle stream function is a constant, the following equation applies for the trajectory of particles with a given electrical mobility, shown as:

$$\Delta\psi = -Z_p \Delta\Phi \tag{10}$$

The limiting streamlines, $\psi_1$ and $\psi_2$ (shown in FIG. 29) form two boundaries which contains the entire volumetric aerosol flow in the mini-disk classifier. The volumetric flow rate, Q may be expressed as follows:

$$Q = 2\pi(\psi_1 - \psi_2) \tag{11}$$

Assume that the particle concentration profile at the aerosol entrance is uniformly distributed between two limiting streamlines. When a voltage is applied to the middle disk, the resulting electrical field deflects the charged particles toward the top grounded plate. From Equation (10), $$\psi^* = \psi_1 + Z_p \Delta\Phi \tag{12}$$

$$\Delta\Phi = \int_0^{r_o} -rE_z dr = -\frac{r_o^2}{2}\frac{V}{2b} \tag{13}$$

where $r_o$, as shown in FIG. 29, is the radius of the small orifices' location on the middle disk; 2b is the height of the flow chamber; and V is the applied voltage. Equations (12) and (13) indicate that, when a positive voltage V is applied on the middle disk, positively charged particles with electrical mobility $Z_p$ and collected on the top grounded plate were initially located between the streamlines $\psi_1$ and $\psi^*$.

The condition for particles penetration may be defined by Equation (14), as follows:

$$P = 1 - \frac{\psi_1 - \psi^*}{\psi_1 - \psi_2} \tag{14}$$

Substituting Equations (11), (12), and (13) into Equation (14) the particle penetration, P, through the disk precipitation zone may be described as:

$$P = 1 - K_1 V \tag{15}$$

$$K_1 = \frac{\pi r_o^2}{2bQ}Z_p \tag{16}$$

Note that the particle penetration is independent of the detailed flow profile in the mini-disk classifier in an embodiment, as long as the flow remains steady and laminar.

The assumptions of a steady, axisymmetric laminar flow and no radial component to the electrical field may not reflect the actual conditions in practice. An empirical coefficient is thus included into Equation (16) to account for the discrepancy between ideal and real conditions:

$$K_1 = \frac{\pi r_o^2}{2bQ\alpha_1}Z_p \tag{17}$$

where $\alpha_1$ is the empirical coefficient, which will be close to 1.0 when the flow and electrical field are close to the assumed values.

Figure 30:
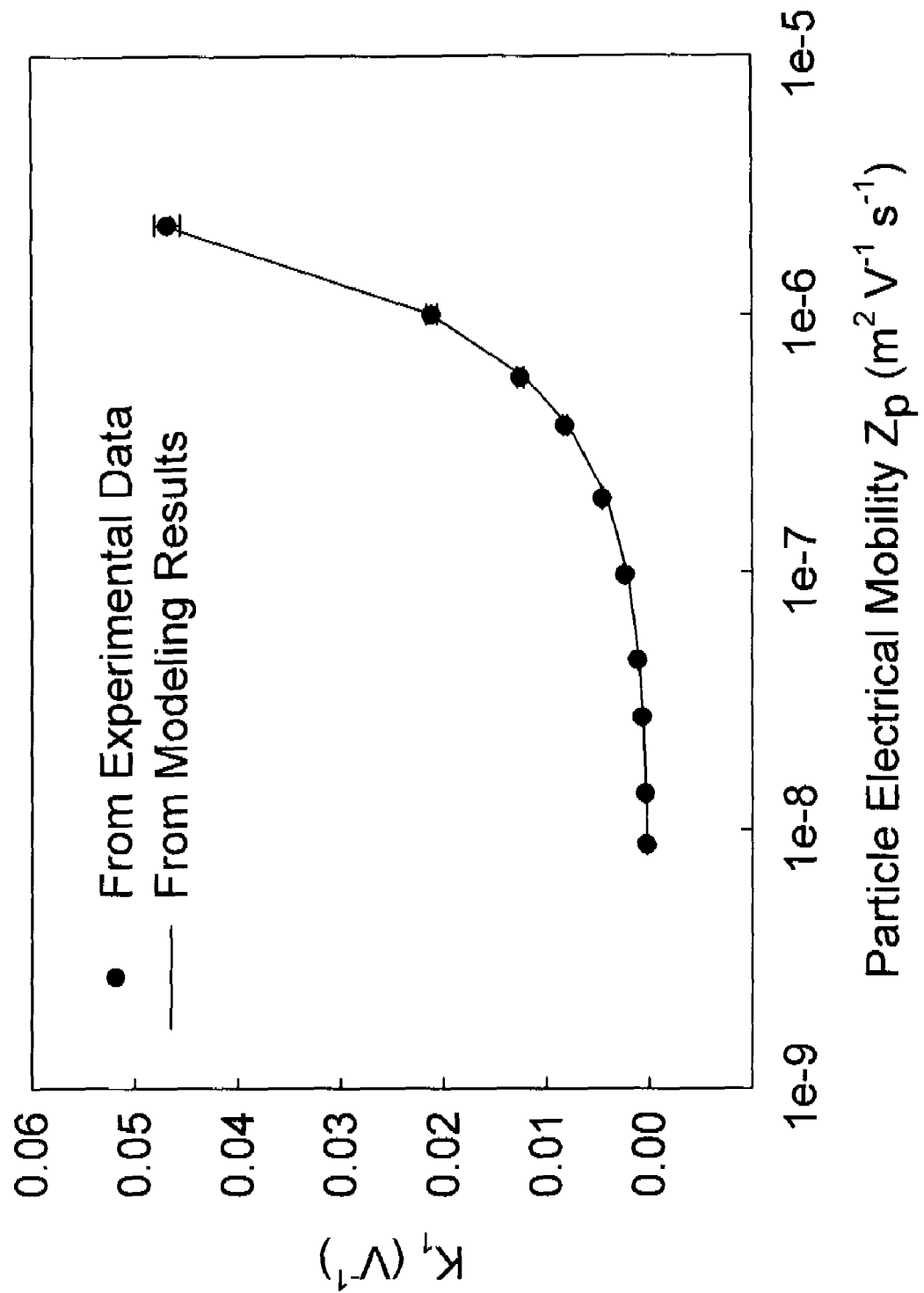
FIG. 30 is a graph illustrating fitting the derived model of $K_1$ with experimental data of the mini-disk classifier shown in FIGS. 18-22 with a flowrate of 0.3 lpm.

Equation (17) is then used to fit the particle cutoff curves given in FIG. 27, using a single flow chamber for charged particle precipitation. Since the curve for each particle size is linear, the slope, $K_1$, may be retrieved from the experimental data. FIG. 30 shows the comparison of the $K_1$ values from both experimental data and the model calculation, as a function of test particle electrical mobility. It is found that the experimental slope, $K_1$, is well fitted with that predicted by the model when the empirical factor, $\alpha_1$, is set as 0.95, indicating the validity of the model as well as its assumptions.

Figure 31:
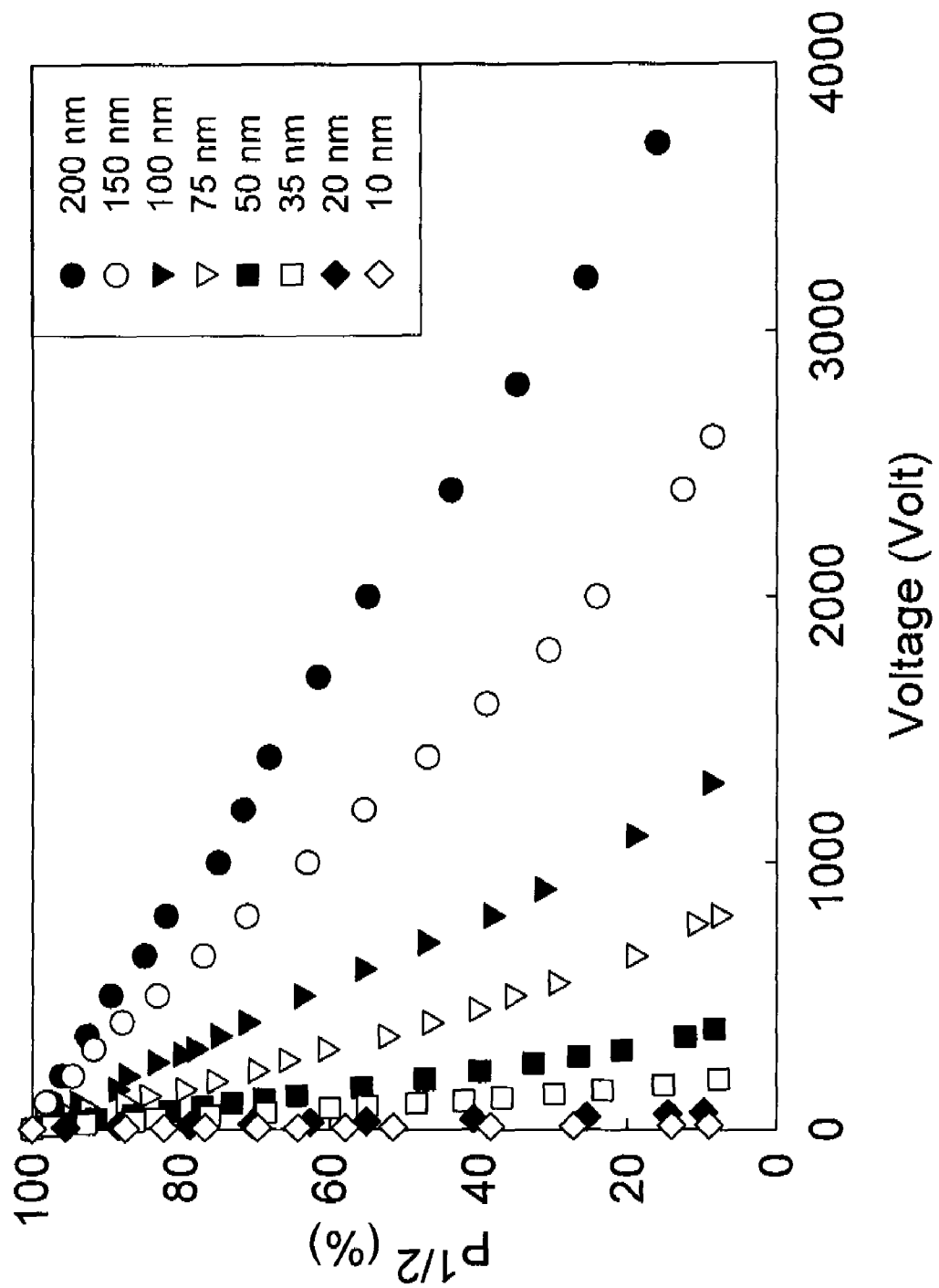
FIG. 31 is a graph illustrating the ratio of $P^{1/2}$ against an applied voltage for experimental data on the dual chamber precipitation operation of the mini-disk classifier shown in FIGS. 18-22 with a flowrate of 0.3 lpm.
Figure 32:
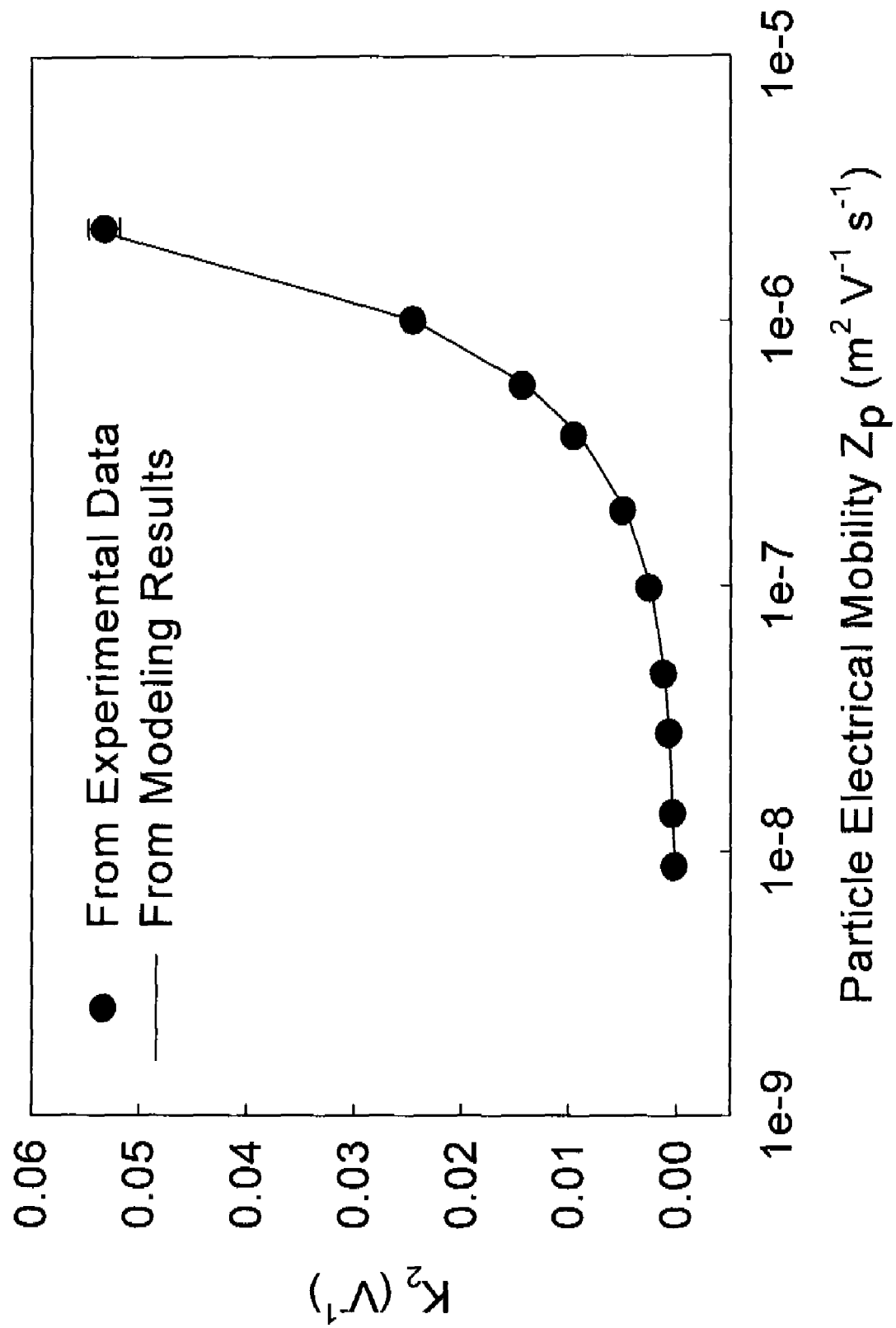
FIG. 32 is a graph illustrating fitting the model of $K_2$ with experimental data of the mini-disk classifier shown in FIGS. 18-22 with a flowrate of 0.3 lpm.

For operation using dual chamber precipitation, the penetration of charged particles through the device is described as follows, based on the assumption of remixing into a uniform particle distribution in the small orifices between the upper and lower flow chambers:

$$P(1 - K_2 V)^2 \tag{18}$$

$$K_2 = \frac{\pi r_o^2}{2bQ\alpha_2}Z_p \tag{19}$$

where $K_2$ is the characteristic slope of particle precipitation for the cutoff curves, and $\alpha_2$ is the empirical factor. From Equation (19), $P^{1/2}$ should be linearly related to applied voltage with the slope of $K_2$. FIG. 31 shows the square root of the experimental particle penetration, $P^{1/2}$, as a function of applied voltage. The linear relationship is clearly demonstrated in the figure. The values of $K_2$ for different particle sizes may be obtained from the slopes given in FIG. 31. FIG. 32 shows the comparison of experimental and modeled $K_2$ values, as the function of particle electrical mobility. It is found that the proposed model may well fit the experimental $K_2$ values at different particle sizes when the empirical factor, $\alpha_2$, is set at 0.82.

Figure 33:
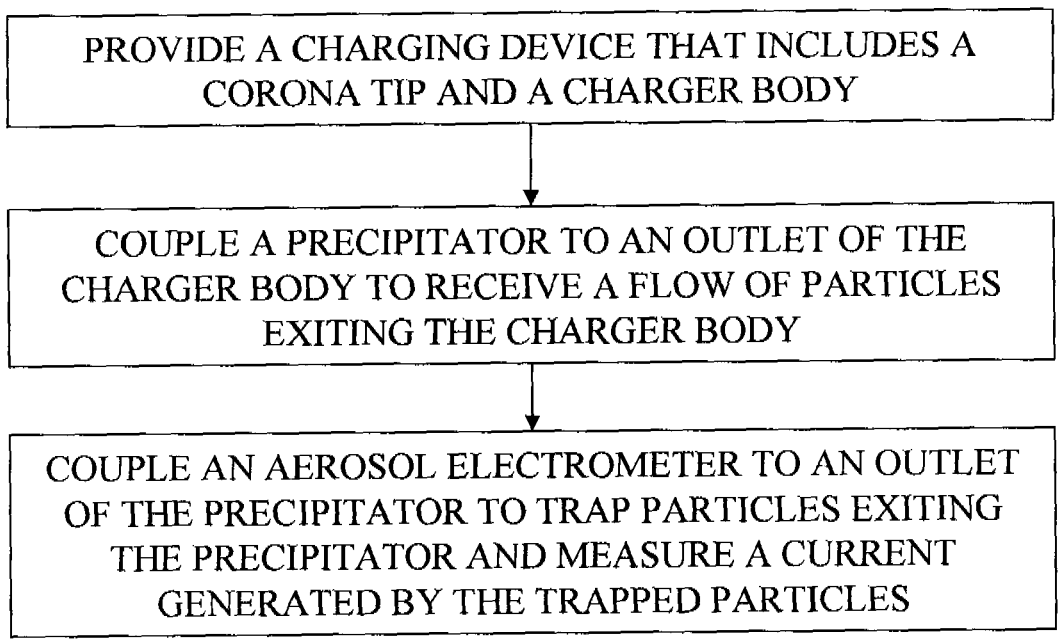
FIG. 33 is a flowchart illustrating an exemplary method for assembling a mini-nanoparticle sizer, such as those shown in FIGS. 1 and 2.
Figure 34:
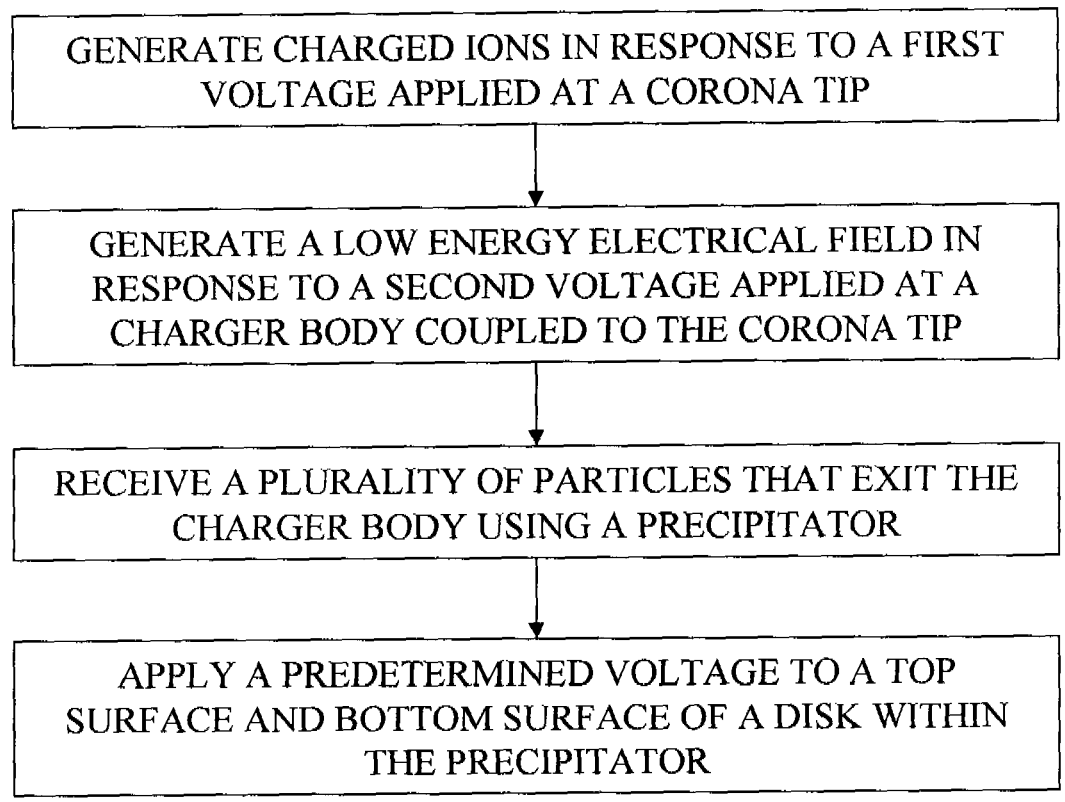
FIG. 34 is a flowchart illustrating an exemplary method for measuring particle size distribution using the mini-nanoparticle sizers shown in FIGS. 1 and 2.

FIG. 33 is a flowchart illustrating an exemplary method for assembling a particle size measurement device, such as those shown in FIGS. 1 and 2. In the exemplary embodiment, and referring to FIGS. 1 and 2, a charging device is provided. The charging device includes a corona tip and a charger body. As described in greater detail above, the corona tip generates positive ions in response to an applied positive voltage, and the charger body generates a low energy electrical field in response to an applied negative voltage in order to channel the positive ions out of the charging device in a direction. Moreover, the corona tip and the charger body are arranged relative to each other in order to direct a flow of a plurality of particles through the low energy electrical field in a substantially parallel direction relative to the direction of the positive ions channeling out of the charging device.

In the exemplary embodiment, a precipitator is then coupled to an outlet of the charging device in order to receive the plurality of particles exiting the charging device. The precipitator includes a disk having a top surface and an opposite bottom surface. A predetermined voltage is applied on the top and bottom surfaces to precipitate the plurality of particles.

In some embodiments, the method also includes coupling an aerosol electrometer to an outlet of the precipitator. As described above, the aerosol electrometer includes a filter and an electrometer. The filter traps particles exiting the precipitator. The electrometer measures a current generated by the trapped particles. Moreover, in other embodiments, the charging device and the precipitator are encapsulated within a metal filter casing. The metal filter casing, as described above, is coupled to an electrometer such that a current generated by the charged particles exiting the precipitator is measured by the electrometer.

FIG. 34 is a flowchart illustrating an exemplary method for measuring particle size distribution using a particle size measurement device, such as those shown in FIGS. 1 and 2. In the exemplary embodiment, and referring to FIGS. 1 and 2, positive ions are generated in response to an applied positive voltage using a corona tip within a charging device. In some embodiments, positive ions are generated by applying the positive voltage to the corona tip in order to trigger a corona between the corona tip and a metal mesh. Moreover, in the exemplary embodiment, a low energy electrical field is generated in response to an applied negative voltage to a charger body coupled to the corona tip within the charging device in order to channel the positive ions out of the charging device in a direction. The corona tip and the charger body are arranged relative to each other in order to direct a flow of a plurality of particles through the low energy electrical field in a substantially parallel direction relative to the direction of the positive ions being channeled out of the charging device.

In the exemplary embodiment, the plurality of particles from the charging device are received in a precipitator that includes a disk having a top surface and an opposite bottom surface. A predetermined voltage is applied on the top surface and the bottom surface to precipitate the plurality of particles. In some embodiments, the precipitator includes an upper plate and a lower plate with the disk arranged between the upper and lower plates. In such embodiments, an electrical field is generated between the upper plate and the disk by applying a voltage to the disk. Alternatively, the electrical field may be generated between the lower plate and the disk by applying the voltage to the disk. In the exemplary embodiment, when the particles enter the precipitator after exiting the charging device, the particles are deflected by the electrical field such that particles having a sufficiently high electrical mobility are precipitated.

In some embodiments, the particle size measurement device also includes an aerosol electrometer. In such embodiments, the particles exiting the precipitator through an outlet of the precipitator are detected by the aerosol electrometer. The particles are trapped within the aerosol electrometer by a filter and a current generated by the trapped particles is measured by an electrometer. A particle number concentration is determined, based on the measured current and a known charge distribution of the trapped particles.

As described herein, embodiments of the invention provide a low-cost solution for applications needing the spatially distributed measurement or personal exposure monitoring of nanoparticles. Despite its compact size, the device provides satisfactory penetration for charged particles. The design of the device allows it to be operated utilizing one or both flow chambers between the middle disk and top/bottom plates for particle precipitation. Both operations work very well in differentiating particle sizes by electrical mobility. The performance of the classifier when operated at a fixed flowrate was experimentally characterized by the particle cutoff curves (e.g., the penetration versus applied voltage). Semi-empirical models describe the particle cutoff curves for both operational conditions. Dual chamber precipitation reduces the voltage requirement to remove all particles of a given electrical mobility. The particle cutoff curves under such an operation are not strictly linear. Modeling results indicate that the nonlinearity is probably a result of the aerosol mixing and redistribution when it moves between the flow chambers.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

The terminology herein is used to describe embodiments of the invention, but their usage does not delimit the invention.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. An apparatus for measuring particle size distribution, said apparatus comprising:

a charging device comprising a corona tip and a charger body, said corona tip configured to generate charged ions in response to a first applied voltage, said charger body configured to generate an electrical field in response to a second applied voltage to channel the charged ions out of said charging device in a direction, wherein the second applied voltage is lower than the first applied voltage, said corona tip and said charger body being arranged coaxially relative to each other to direct a flow of a plurality of particles through the electrical field in a substantially parallel direction relative to the direction of the charged ions channeling out of said charging device; and a precipitator for receiving the plurality of particles from the charging device, said precipitator comprising a disk comprising a top surface and an opposite bottom surface, wherein a predetermined voltage is applied to said top surface and said bottom surface to precipitate the plurality of particles, wherein said precipitator further comprises an upper plate and a lower plate, said disk being arranged between said upper and lower plates.

2. An apparatus in accordance with claim 1, wherein said corona tip is positioned at a center point of a semi-spherical metal mesh such that the first applied voltage applied to said corona tip triggers a corona between said corona tip and said metal mesh in order to generate the charged ions.

3. An apparatus in accordance with claim 1, wherein at least one of said upper plate and said lower plate is coupled to ground in order to generate an electrical field between the grounded plate and said disk when the predetermined voltage is applied to said disk.

4. An apparatus in accordance with claim 3, wherein the plurality of particles are deflected by the electrical field upon entering said precipitator such that particles having a sufficiently high electrical mobility are precipitated.

5. An apparatus in accordance with claim 4, wherein said disk comprises a plurality of orifices positioned at an edge of said disk to facilitate precipitation of the particles having a sufficiently high electrical mobility.

6. An apparatus in accordance with claim 1, wherein said disk comprises a plurality of disks.

7. An apparatus in accordance with claim 1, further comprising an aerosol electrometer coupled to an outlet of said precipitator, said aerosol electrometer configured to detect particles exiting said precipitator.

8. An apparatus in accordance with claim 7, wherein said aerosol electrometer comprises a filter and an electrometer, said filter configured to trap the particles exiting said precipitator, said electrometer configured to measure a current generated by the trapped particles.

9. A method of assembling a particle size measurement device, said method comprising:
providing a charging device that includes a corona tip and a charger body, wherein the corona tip is configured to generate charged ions in response to a first applied voltage, the charger body being configured to generate an electrical field in response to a second applied voltage to channel the charged ions out of the charging device in a direction, wherein the second applied voltage is lower than the first applied voltage, the corona tip and the charger body being arranged coaxially relative to each other to direct a flow of a plurality of particles through the electrical field in a substantially parallel direction relative to the direction of the charged ions channeling out of the charging device; and
coupling a precipitator to an outlet of the charging device to receive the plurality of particles, the precipitator including a disk having a top surface and an opposite bottom surface, wherein a predetermined voltage is applied to the top and bottom surfaces to precipitate the plurality of particles,
wherein said precipitator further comprises an upper plate and a lower plate, said disk being arranged between said upper and lower plates.

10. A method in accordance with claim 9, further comprising coupling an aerosol electrometer to an outlet of the precipitator, the aerosol electrometer including a filter and an electrometer, the filter configured to trap particles exiting the precipitator, the electrometer configured to measure a current generated by the trapped particles.

11. A method in accordance with claim 9, further comprising encapsulating the charging device and the precipitator within a metal filter casing coupled to an electrometer such that a current generated by charged particles exiting the precipitator generates a current that is measured by the electrometer.

12. A method for measuring particle size distribution, said method comprising:
generating charged ions in response to a first voltage applied to a corona tip within a charging device;
generating an electrical field in response to a second voltage applied to a charger body coupled to the corona tip within the charging device in order to channel the charged ions out of the charging device in a direction, wherein the second applied voltage is lower than the first applied voltage, the corona tip and the charger body being arranged coaxially relative to each other to direct a flow of a plurality of particles through the electrical field in a substantially parallel direction relative to the direction of the charged ions channeling out of the charging device;
receiving the plurality of particles from the charging device in a precipitator that includes a disk having a top surface and an opposite bottom surface; and
applying a predetermined voltage to the top surface and the bottom surface to precipitate the plurality of particles,
wherein said precipitator further comprises an upper plate and a lower plate, said disk being arranged between said upper and lower plates.

13. A method in accordance with claim 12, wherein generating charged ions comprises applying the first voltage to the corona tip in order to trigger a corona between the corona tip and a metal mesh.

14. A method in accordance with claim 12, further comprising generating an electrical field between one of the upper plate and the lower plate, and the disk by applying the predetermined voltage to the disk.

15. A method in accordance with claim 14, further comprising deflecting the plurality of particles by the electrical field upon entering the precipitator such that particles having a sufficiently high electrical mobility are precipitated.

16. A method in accordance with claim 12, further comprising detecting the particles exiting the precipitator using an aerosol electrometer coupled to an outlet of the precipitator.

17. A method in accordance with claim 16, further comprising trapping the particles exiting the precipitator using a filter and measuring a current generated by the trapped particles.

18. A method in accordance with claim 17, further comprising determining a particle number concentration based on the current and a known charge distribution of the trapped particles.

* * * * *